(12) United States Patent
Collins et al.

(10) Patent No.: US 10,259,806 B2
(45) Date of Patent: Apr. 16, 2019

(54) 5-[[4-[[MORPHOLIN-2-YL]METHYLAMINO]-5-(TRIFLUOROMETHYL)-2 PYRIDYL]AMINO]PYRAZINE-2-CARBONITRILE AND THERAPEUTIC USES THEREOF

(71) Applicant: Cancer Research Technology Limited, London (GB)

(72) Inventors: Ian Collins, Sutton (GB); Thomas Peter Matthews, Sutton (GB); Tatiana Faria Da Fonseca Mchardy, Sutton (GB); James Osborne, Saffron Walden (GB); Michael Lainchbury, Harlow (GB); Michael Ian Walton, Sutton (GB); Michelle Dawn Garrett, Sutton (GB)

(73) Assignee: CANCER RESEARCH TECHNOLOGY LIMITED, London (GB)

( * ) Notice: Subject to any disclaimer, the term of this patent is extended or adjusted under 35 U.S.C. 154(b) by 0 days.

(21) Appl. No.: 15/587,270

(22) Filed: May 4, 2017

(65) Prior Publication Data
US 2018/0022739 A1   Jan. 25, 2018

Related U.S. Application Data

(63) Continuation of application No. 14/396,338, filed as application No. PCT/GB2013/051233 on May 14, 2013, now Pat. No. 9,663,503.

(60) Provisional application No. 61/647,200, filed on May 15, 2012.

(51) Int. Cl.
| | |
|---|---|
| C07D 413/14 | (2006.01) |
| C07D 413/02 | (2006.01) |
| C07D 401/12 | (2006.01) |
| A61K 9/00 | (2006.01) |
| A61K 31/4745 | (2006.01) |
| A61K 31/5377 | (2006.01) |
| A61K 31/7068 | (2006.01) |
| A61K 45/06 | (2006.01) |

(52) U.S. Cl.
CPC .......... *C07D 413/14* (2013.01); *A61K 9/0053* (2013.01); *A61K 31/4745* (2013.01); *A61K 31/5377* (2013.01); *A61K 31/7068* (2013.01); *A61K 45/06* (2013.01); *C07D 401/12* (2013.01); *C07D 413/02* (2013.01)

(58) Field of Classification Search
None
See application file for complete search history.

(56) References Cited

U.S. PATENT DOCUMENTS

| | | | |
|---|---|---|---|
| 3,773,778 | A | 11/1973 | Hoehn et al. |
| 8,058,045 | B2 | 11/2011 | Collins et al. |
| 8,367,658 | B2 | 2/2013 | Collins et al. |
| 8,530,468 | B2 | 9/2013 | Collins et al. |

(Continued)

FOREIGN PATENT DOCUMENTS

| | | |
|---|---|---|
| EA | 200800441 | 8/2008 |
| JP | 2010-540610 | 12/2010 |

(Continued)

OTHER PUBLICATIONS

Vippagunta et al., "Crystalline Solids" Advanced Drug Delivery Reviews (2001) vol. 48 pp. 3-26.*

(Continued)

*Primary Examiner* — Eric Olson
(74) *Attorney, Agent, or Firm* — Fenwick & West LLP

(57) ABSTRACT

The present invention pertains generally to the field of therapeutic compounds. More specifically the present invention pertains to 5-[[4-[[morpholin-2-yl]methylamino]-5-(trifluoromethyl)-2-pyridyl]amino]pyrazine-2-carbonitrile compounds (referred to herein as "TFM compounds") which, inter alia, inhibit Checkpoint Kinase 1 (CHK1) kinase function. The present invention also pertains to pharmaceutical compositions comprising such compounds, and the use of such compounds and compositions, both in vitro and in vivo, to inhibit CHK1 kinase function, and in the treatment of diseases and conditions that are mediated by CHK1, that are ameliorated by the inhibition of CHK1 kinase function, etc., including proliferative conditions such as cancer, etc., optionally in combination with another agent, for example, (a) a DNA topoisomerase I or II inhibitor; (b) a DNA damaging agent; (c) an antimetabolite or a thymidylate synthase (TS) inhibitor; (d) a microtubule targeted agent; (e) ionizing radiation; (f) an inhibitor of a mitosis regulator or a mitotic checkpoint regulator; (g) an inhibitor of a DNA damage signal transducer; or (h) an inhibitor of a DNA damage repair enzyme.

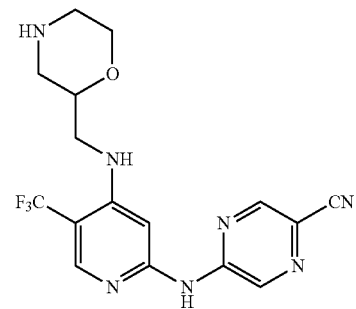

16 Claims, No Drawings
Specification includes a Sequence Listing.

(56) References Cited

U.S. PATENT DOCUMENTS

| | | | |
|---|---|---|---|
| 8,618,121 | B2 | 12/2013 | Collins et al. |
| 9,040,540 | B2 | 5/2015 | Collins et al. |
| 9,403,797 | B2 | 8/2016 | Collins et al. |
| 2005/0215556 | A1 | 9/2005 | Lin et al. |
| 2010/0210639 | A1 | 8/2010 | Collins et al. |
| 2010/0311730 | A1 | 12/2010 | Collins et al. |
| 2010/0331328 | A1 | 12/2010 | Collins et al. |
| 2012/0040967 | A1 | 2/2012 | Collins et al. |
| 2014/0315925 | A1 | 10/2014 | Collins et al. |
| 2015/0225372 | A1 | 8/2015 | Collins et al. |

FOREIGN PATENT DOCUMENTS

| | | |
|---|---|---|
| RU | 2009110255 A | 9/2010 |
| WO | WO 1995-019970 A1 | 7/1995 |
| WO | WO 1997-002266 A1 | 1/1997 |
| WO | WO 2003-032984 A1 | 4/2003 |
| WO | WO 2003-035065 A1 | 5/2003 |
| WO | WO 2003-037898 A1 | 5/2003 |
| WO | WO 2003-093297 A2 | 11/2003 |
| WO | WO 2003-101444 A1 | 12/2003 |
| WO | WO 2005-011597 A2 | 2/2005 |
| WO | WO 2005-034869 A2 | 4/2005 |
| WO | WO 2005-037285 A1 | 4/2005 |
| WO | WO 2005-037825 A2 | 4/2005 |
| WO | WO 2005-047294 A1 | 5/2005 |
| WO | WO 2005-121126 A1 | 12/2005 |
| WO | WO 2006-039718 A2 | 4/2006 |
| WO | WO 2006-116733 A2 | 11/2006 |
| WO | WO 2007-000240 A1 | 1/2007 |
| WO | WO 2007-041712 A1 | 4/2007 |
| WO | WO 2007-044779 A1 | 4/2007 |
| WO | WO 2008-077554 A1 | 7/2008 |
| WO | WO 2008-115369 A2 | 9/2008 |
| WO | WO 2008-117050 A1 | 10/2008 |
| WO | WO 2009-004329 A1 | 1/2009 |
| WO | WO 2009-044162 A1 | 4/2009 |
| WO | WO 2009-103966 A1 | 8/2009 |
| WO | WO 2013-068755 A1 | 5/2013 |
| WO | WO 2013-171470 A1 | 11/2013 |

OTHER PUBLICATIONS

Lieberman et al., "Pharmaceutical Dosage Forms, vol. 2" Published 1990 by Marcel Dekker, Inc, pp. 462-472.*
Jain et al., "Polymorphism in Pharmacy" Indian Drugs (1986) vol. 23 No. 6 pp. 315-329.*
Braga et al., "Making Crystals from Crystals: a green route to crystal engineering and polymorphism" Chemical Communications (2005) pp. 3635-3645.*
Balint et al., 2001, "Activation and activities of the p53 tumour suppressor protein," Br. J. Cancer, vol. 85, pp. 1813-1823.
Bartek et al., 2003, "Chk1 and Chk2 kinases in checkpoint control and cancer," Cancer Cell, vol. 3, pp. 421-429.
Brooks et al., 2012, "A potent chk1 inhibitor is selectively toxic in melanomas with high levels of replicative stress," Oncogene, vol. 32, pp. 788-796.
Carson et al., 1995, "Cancer progression and p53," Lancet, vol. 346, pp. 1009-1011.
Cavelier et al., 2009, "Constitutive activation of the DNA damage signaling pathway in acute myeloid leukemia with complex karyotype: Potential importance for checkpoint targeting therapy," Cancer Res., vol. 69, pp. 8652-8661.
Cole et al., 2011 "RNAi screen of the protein kinome identifies checkpoint kinase 1 (chk1) as a therapeutic target in neuroblastoma," Proc. Natl. Acad. Sci. U.S.A., vol. 108, pp. 3336-3341.
Davies et al., 2011, "Single-agent inhibition of chk1 is antiproliferative in human cancer cell lines in vitro and inhibits tumor xenograft growth in vivo," Oncol. Res., vol. 19, pp. 349-363.
Di Micco et al., 2006, "Oncogene-induced senescence is a DNA damage response triggered by DNA hyper-replication," Nature, vol. 444, pp. 638-642.

Dixon et al., 2002, "Therapeutic exploitation of checkpoint defects in cancer cells lacking p53 function," Cell Cycle, vol. 1, pp. 362-368.
Durola et al., 2007, "A New Family of Biisoquinoline Chelates", Eur. J. Org. Chem., Issue 1, pp. 125-135.
Ferrao et al., 2011, "Efficacy of chk inhibitors as single agents in myc-driven lymphoma cells," Oncogene, vol. 31, pp. 1661-1672.
Gabriel et al., 1908, "Ubergang von der Chinoxalin zur Pyrazinreihe", Berichte der Deutschen Chemischen Gesellschaft, vol. 40, pp. 4850-4860 (with Engilsh Abstract).
Greenblatt et al., 1994, "Mutations in the p53 tumor suppressor gene: clues to cancer etiology and molecular pathogenesis," Cancer Res., vol. 54, pp. 4855-4878.
Guzi et al., 2011, "Targeting the replication checkpoint using SCH 900776, a potent and functionally selective CHK1 inhibitor identified via high content screening," Mol. Cancer Ther., vol. 10, pp. 591-602.
Hoglund et al., 2011, "Therapeutic Implications for the Induced Levels of Chk1 in Myc-Expressing Cancer Cells," Clin. Cancer Res., vol. 17, pp. 7067-7079.
Intellectual Property Australia, Examination Report, Australian Patent Application No. 2012335409, dated Jul. 13, 2016, 2 Pages.
Intellectual Property Australia, Examination Report, Australian Patent Application No. 2013261605, dated Oct. 5, 2016, 2 Pages.
International Preliminary Report on Patentability for Application No. PCT/GB2013/051233 dated Nov. 18, 2014.
Ioannidis et al., "Discovery of pyrazol-3-ylamino pyrazines as novel JAK2 inhibitors", Bioorg. & Med. Chem. Lett., 2009, vol. 19, pp. 6524-6528.
Itoh et al., 2002, "Efficient synthesis of substituted 2-aminopyrazines: $FeCl_3$-promoted condensation of hydroxyiminoketones with anninoacetonitriles", Tetrahedron Lett., vol. 43, pp. 9287-9290.
Lainchbury et al., 2011, "Checkpoint kinase inhibitors: a patent review (2009-2010)", Exp. Opin. Ther. Pat., vol. 21, No. 8, pp. 1911-1210.
Lainchbury et al., Oct. 19, 2012, "Discovery of 3-Alkoxyannino-5-(pyridin-2-ylannino)pyrazine-2-carbonitriles as Selective, Orally Bioavailable CHK1 Inhibitors", J. Med. Chem., vol. 55, No. 22, pp. 10229-10240.
Li et al., 2007, "Synthesis and in-vitro biological activity of macrocyclic urea CHK1 inhibitors", Bioorg. & Med. Chem. Lett., vol. 17, pp. 6499-6504.
Liu et al., 2000, "Chk1 is an essential kinase that is regulated by Atr and required for the G(2)/M DNA damage checkpoint," Genes Dev., vol. 14, pp. 1448-1459.
Murga et al., 2011, "Exploiting oncogene-induced replicative stress for the selective killing of Myc-driven tumors," Nat. Struct. Mol. Biol., vol. 18, pp. 1331-1335.
Russian Patent Office, Official Action, Russian Patent Application No. 2014121334, dated Sep. 1, 2016, 6 Pages.
Sanchez et al., 1997, "Conservation of the Chk1 checkpoint pathway in mammals: linkage of DNA damage to Cdk regulation through Cdc25," Science, vol. 277, pp. 1497-1501.
Sorensen et al., 2005, "Cell-cycle checkpoint kinase Chk1 is required for mammalian homologous recombination repair," Nat. Cell Biol., vol. 7, pp. 195-201.
Syljuasen et al., 2015, "Targeting lung cancer through inhibition of checkpoint kinases", Frontiers in Genetics, vol. 6, Article 70, pp. 1-11.
Tao et al., 2006, "Chk1 inhibitors for novel cancer treatment," Anti-Cancer Agents in Medicinal Chemistry, vol. 6, pp. 377-388.
Tao et al., 2007, "Macrocyclic ureas as potent and selective CHK1 inhibitors: an improved synthesis, kinome profiling, structure-activity relationships, and preliminary pharmacokinetics," Bioorg. Med. Chem. Lett., vol. 17, pp. 6593-6601.
Tao et al., 2007, "Structure-based design, synthesis, and biological evaluation of potent and selective macrocyclic checkpoint kinase 1 inhibitors," J. Med. Chem., vol. 50, pp. 1514-1527.
Tse et al., 2007, "CHIR-124, a Novel Potent Inhibitor of Chk1, Potentiates the Cyctotoxicity of Topoisomerase I Poisons In vitro and In vivo," Clin. Cancer Res. vol. 13(2) pp. 591-602.

(56) References Cited

OTHER PUBLICATIONS

Ugarkar et al., 2000, "Adenosine Kinase Inhibitors. 1. Synthesis, Enzyme Inhibition, and Antiseizure Activity of 5-Iodotubercidin Analogues," Journal of Medicinal Chemistry, vol. 43, pp. 2883-2893.

Walton et al., 2010, "The Preclinical Pharmacology and Therapeutic Activity of the Novel CHK1 Inhibitor SAR-020106", Molecular Cancer Therapeutics, vol. 9(1), pp. 89-100.

Walton et al., 2012, "CCT244747 Is a Novel Potent and Selective CHK1 Inhibitor with Oral Efficacy Alone and in Combination with Genotoxic Anticancer Drugs", Clin. Cancer Res., vol. 18, pp. 5650-5661.

Wang et al., 1996, "UCN-01: a potent a brogator of G2 checkpoint function in cancer cells with disrupted p53," J. Natl. Cancer Inst., vol. 8, pp. 956-965.

Weinert et al., 1989, "Control of G2 delay by the rad9 gene of *Saccharomyces cerevisiae*," J. Cell Sci. Suppl., vol. 12, pp. 145-148.

White et al., 1967, "Gattermann reaction of 3,5-dimethoxyphenylacetonitrile. Synthesis of 6,8-dioxyisoquinolines", J. Org. Chem., vol. 32, pp. 2689-2692.

Xiao et al., 2006, "Differential roles of checkpoint kinase 1, checkpoint kinase 2, and mitogen-activated protein kinase-activated protein kinase 2 in mediating DNA damage-induced cell cycle arrest: implications for cancer therapy," Mol. Cancer Ther., vol. 5, pp. 1935-1943.

Zachos et al., 2003, "Chk1-deficient tumour cells are viable but exhibit multiple checkpoint and survival defects," EMBO J., vol. 22, pp. 713-723.

Zhao et al., 2002, "Disruption of the checkpoint kinase 1/cell division cycle 25A pathway abrogates ionizing radiation-induced S and G2 checkpoints," Proc. Natl. Acad. Sci. USA, vol. 99, pp. 14795-14800.

European Patent Office, Extended European Search Report, European Patent Application No. 17152400.0, dated Jun. 2, 2017, seven pages.

\* cited by examiner

5-[[4-[[MORPHOLIN-2-YL]METHYLAMINO]-5-(TRIFLUOROMETHYL)-2 PYRIDYL] AMINO]PYRAZINE-2-CARBONITRILE AND THERAPEUTIC USES THEREOF

RELATED APPLICATIONS

This application is a continuation of U.S. application Ser. No. 14/396,338, filed Oct. 22, 2014, now U.S. Pat. No. 9,663,503 issued May 30, 2017, which is the National Stage of International Application No. PCT/GB2013/051233, filed May 14, 2013. International application number PCT/GB2013/051233 claims the benefit of U.S. patent application No. 61/647,200 filed May 15, 2012, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Oct. 2, 2017, is named 36988US_CRF_sequencelisting.txt and is 821 bytes in size.

TECHNICAL FIELD

The present invention pertains generally to the field of therapeutic compounds. More specifically the present invention pertains to 5-[[4-[[morpholin-2-yl]methylamino]-5-(trifluoromethyl)-2-pyridyl]amino]pyrazine-2-carbonitrile compounds (referred to herein as "TFM compounds") which, inter alia, inhibit Checkpoint Kinase 1 (CHK1) kinase function. The present invention also pertains to pharmaceutical compositions comprising such compounds, and the use of such compounds and compositions, both in vitro and in vivo, to inhibit CHK1 kinase function, and in the treatment of diseases and conditions that are mediated by CHK1, that are ameliorated by the inhibition of CHK1 kinase function, etc., including proliferative conditions such as cancer, etc., optionally in combination with another agent, for example, (a) a DNA topoisomerase I or II inhibitor; (b) a DNA damaging agent; (c) an antimetabolite or a thymidylate synthase (TS) inhibitor; (d) a microtubule targeted agent; (e) ionising radiation; (f) an inhibitor of a mitosis regulator or a mitotic checkpoint regulator; (g) an inhibitor of a DNA damage signal transducer; or (h) an inhibitor of a DNA damage repair enzyme.

BACKGROUND

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.
Checkpoint Kinase 1 (CHK1)

Progression through the cell division cycle is a tightly regulated process and is monitored at several positions known as cell cycle checkpoints (see, e.g., Weinert and Hartwell, 1989; Bartek and Lukas, 2003). These checkpoints are found in all four stages of the cell cycle; G1, S (DNA replication), G2 and M (Mitosis) and they ensure that key events which control the fidelity of DNA replication and cell division are completed correctly. Cell cycle checkpoints are activated by a number of stimuli, including DNA damage and DNA errors caused by defective replication. When this occurs, the cell cycle will arrest, allowing time for either DNA repair to occur or, if the damage is too severe, for activation of cellular processes leading to controlled cell death.

All cancers, by definition, have some form of aberrant cell division cycle. Frequently, the cancer cells possess one or more defective cell cycle checkpoints, or harbour defects in a particular DNA repair pathway. These cells are therefore often more dependent on the remaining cell cycle checkpoints and repair pathways, compared to non-cancerous cells (where all checkpoints and DNA repair pathways are intact). The response of cancer cells to DNA damage is frequently a critical determinant of whether they continue to proliferate or activate cell death processes and die. For example, tumour cells that contain a mutant form(s) of the tumour suppressor p53 are defective in the G1 DNA damage checkpoint. Thus inhibitors of the G2 or S-phase checkpoints are expected to further impair the ability of the tumour cell to repair damaged DNA.

Many known cancer treatments cause DNA damage by either physically modifying the cell's DNA or disrupting vital cellular processes that can affect the fidelity of DNA replication and cell division, such as DNA metabolism, DNA synthesis, DNA transcription and microtubule spindle formation. Such treatments include for example, radiotherapy, which causes DNA strand breaks, and a variety of chemotherapeutic agents including topoisomerase inhibitors, antimetabolites, DNA-alkylating agents, and platinum-containing cytotoxic drugs. A significant limitation to these genotoxic treatments is drug resistance. One of the most important mechanisms leading to this resistance is attributed to activation of cell cycle checkpoints, giving the tumour cell time to repair damaged DNA. By abrogating a particular cell cycle checkpoint, or inhibiting a particular form of DNA repair, it may therefore be possible to circumvent tumour cell resistance to the genotoxic agents and augment tumour cell death induced by DNA damage, thus increasing the therapeutic index of these cancer treatments.

CHK1 is a serine/threonine kinase involved in regulating cell cycle checkpoint signals that are activated in response to DNA damage and errors in DNA caused by defective replication (see, e.g., Bartek and Lukas, 2003). CHK1 transduces these signals through phosphorylation of substrates involved in a number of cellular activities including cell cycle arrest and DNA repair. Two key substrates of CHK1 are the Cdc25A and Cdc25C phosphatases that dephosphorylate CDK1 leading to its activation, which is a requirement for exit from G2 into mitosis (M phase) (see, e.g., Sanchez et al., 1997). Phosphorylation of Cdc25C and the related Cdc25A by CHK1 blocks their ability to activate CDK1, thus preventing the cell from exiting G2 into M phase. The role of CHK1 in the DNA damage-induced G2 cell cycle checkpoint has been demonstrated in a number of studies where CHK1 function has been knocked out (see, e.g., Liu et al., 2000; Zhao et al., 2002; Zachos et al., 2003).

The reliance of the DNA damage-induced G2 checkpoint upon CHK1 provides one example of a therapeutic strategy for cancer treatment, involving targeted inhibition of CHK1. Upon DNA damage, the p53 tumour suppressor protein is stabilised and activated to give a p53-dependent G1 arrest, leading to apoptosis or DNA repair (Balaint and Vousden, 2001). Over half of all cancers are functionally defective for p53, which can make them resistant to genotoxic cancer treatments such as ionising radiation (IR) and certain forms of chemotherapy (see, e.g., Greenblatt et al., 1994; Carson and Lois, 1995). These p53 deficient cells fail to arrest at the G1 checkpoint or undergo apoptosis or DNA repair, and consequently may be more reliant on the G2 checkpoint for viability and replication fidelity. Therefore abrogation of the G2 checkpoint through inhibition of the CHK1 kinase function may selectively sensitise p53 deficient cancer cells to genotoxic cancer therapies, and this has been demonstrated (see, e.g., Wang et al., 1996; Dixon and Norbury, 2002).

In addition, CHK1 has also been shown to be involved in S phase cell cycle checkpoints and DNA repair by homologous recombination. Thus, inhibition of CHK1 kinase in those cancers that are reliant on these processes after DNA damage, may provide additional therapeutic strategies for the treatment of cancers using CHK1 inhibitors (see, e.g., Sorensen et al., 2005). Furthermore, certain cancers may exhibit replicative stress due to high levels of endogenous DNA damage (see, e.g., Cavalier et al., 2009; Brooks et al., 2012) or through elevated replication driven by oncogenes, for example amplified or overexpressed MYC genes (see, e.g., Di Micco et al. 2006; Cole et al., 2011; Murga et al. 2011). Such cancers may exhibit elevated signalling through CHK1 kinase (see, e.g., Höglund et al., 2011). Inhibition of CHK1 kinase in those cancers that are reliant on these processes, may provide additional therapeutic strategies for the treatment of cancers using CHK1 inhibitors (see, e.g., Cole et al., 2011; Davies et al., 2011; Ferrao et al., 2011).

Recent data using CHK1 selective siRNA supports the selective inhibition of CHK1 as a relevant therapeutic approach, and suggests that combined inhibition with certain other checkpoint kinases provides no additional benefit and may be non-productive (see, e.g., Xiao et al., 2006; Guzi et al., 2011). Small-molecule selective inhibitors of CHK1 kinase function from various chemical classes have been described (see, e.g., Tao et al., 2006).

Known Compounds

Collins et al., 2009a (WO 2009/044162 A1) describes certain compounds of the following formula which inhibit Checkpoint Kinase 1 (CHK1) kinase function, and which are useful in the treatment of, e.g., cancer:

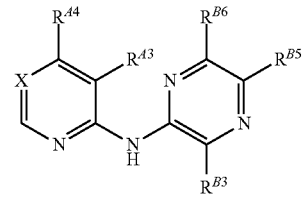

Among the examples in Collins et al., 2009a are the following compounds:

TABLE 1

| # | Reg. No. | Code | Chemical Structure |
|---|---|---|---|
| 1 | 1137477-07-6 | Y-081 | 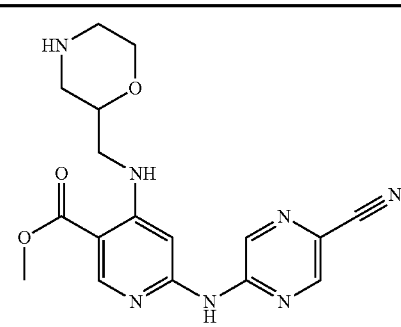 |
| 2 | 1137477-35-0 | Y-102 | 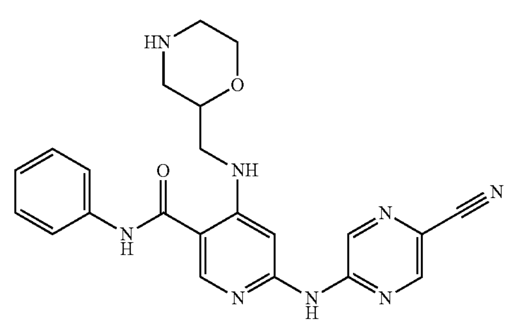 [SMILES: N#Cc1cnc(Nc2cc(NCC3CNCCO3)c(C(=O)Nc3ccccc3)cn2)cn1] |

TABLE 1-continued

| # | Reg. No. | Code | Chemical Structure |
|---|---|---|---|
| 3 | 1168103-91-0 | Y-146 | 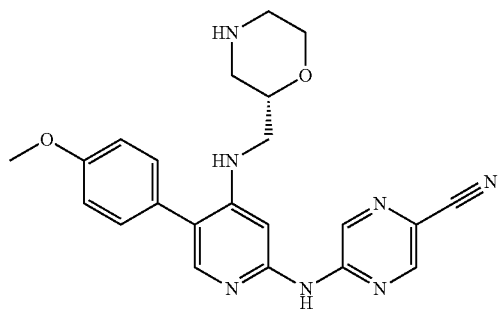 [SMILES: COc1ccc(-c2cnc(Nc3cnc(C#N)cn3)cc2NC[C@@H]2CNCCO2)cc1] |
| 4 | 1137478-38-6 | Y-147 | 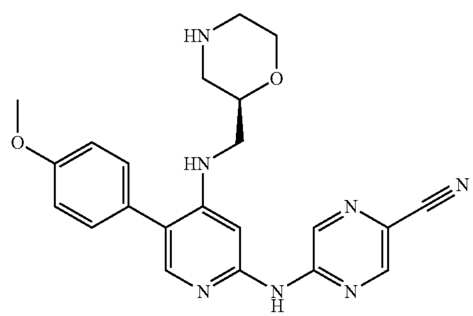 [SMILES: COc1ccc(-c2cnc(Nc3cnc(C#N)cn3)cc2NC[C@H]2CNCCO2)cc1] |
| 5 | 1137478-39-7 | Y-148 | 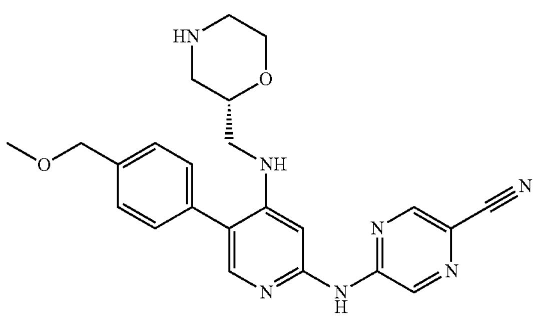 [SMILES: COCc1ccc(-c2cnc(Nc3cnc(C#N)cn3)cc2NC[C@@H]2CNCCO2)cc1] |
| 6 | 1137478-40-0 | Y-149 | 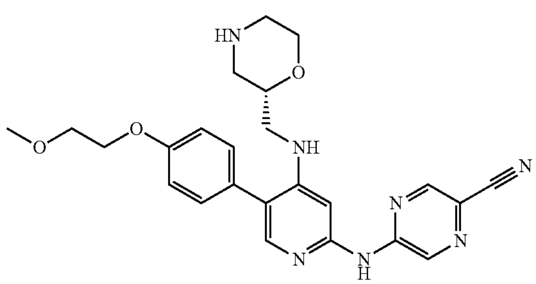 [SMILES: COCCOc1ccc(-c2cnc(Nc3cnc(C#N)cn3)cc2NC[C@@H]2CNCCO2)cc1] |
| 7 | 1137478-41-1 | Y-150 | 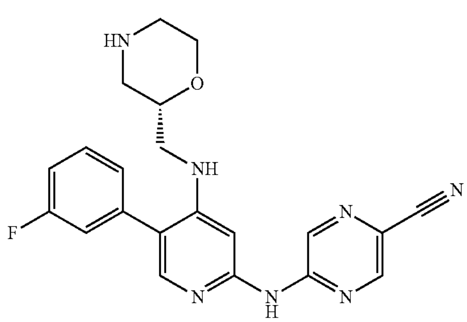 [SMILES: N#Cc1cnc(Nc2cc(NC[C@@H]3CNCCO3)c(-c3cccc(F)c3)cn2)cn1] |

TABLE 1-continued

| # | Reg. No. | Code | Chemical Structure |
|---|----------|------|-------------------|
| 8 | 1137478-44-4 | Y-151 | 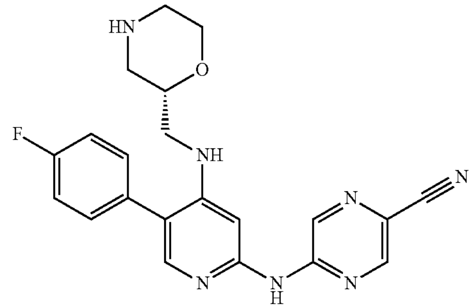 [SMILES: N#Cc1cnc(Nc2cc(NC[C@@H]3CNCCO3)c(-c3ccc(F)cc3)cn2)cn1] |
| 9 | 1137478-45-5 | Y-152 | 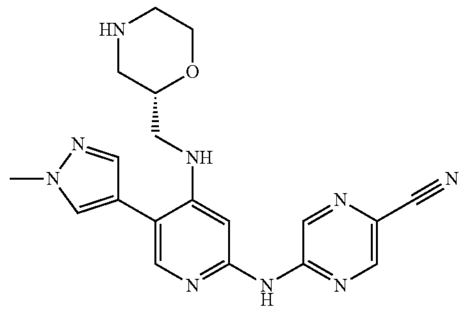 [SMILES: Cn1cc(-c2cnc(Nc3cnc(C#N)cn3)cc2NC[C@@H]2CNCCO2)cn1] |
| 10 | 1137478-46-6 | Y-153 | 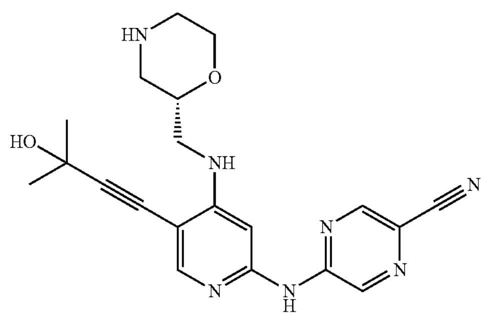 [SMILES: CC(C)(O)C#Cc1cnc(Nc2cnc(C#N)cn2)cc1NC[C@@H]1CNCCO1] |
| 11 | 1137478-47-7 | Y-154 | 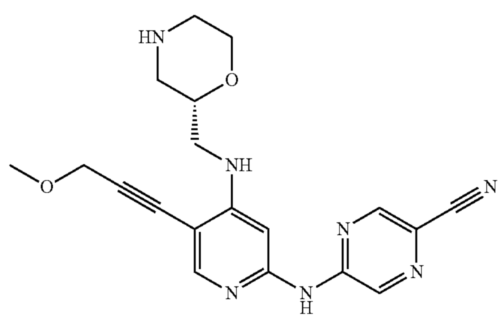 [SMILES: COCC#Cc1cnc(Nc2cnc(C#N)cn2)cc1NC[C@@H]1CNCCO1] |
| 12 | 1137478-48-8 | Y-155 | 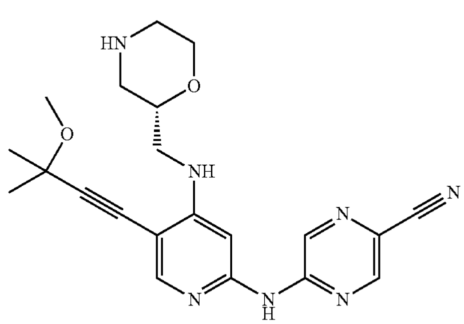 [SMILES: COC(C)(C)C#Cc1cnc(Nc2cnc(C#N)cn2)cc1NC[C@@H]1CNCCO1] |

TABLE 1-continued

| # | Reg. No. | Code | Chemical Structure |
|---|----------|------|---------------------|
| 13 | 1137478-50-2 | Y-156 | 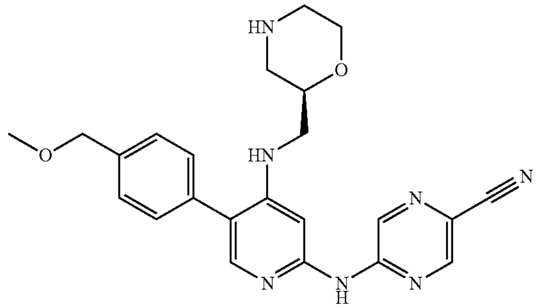 [SMILES: COCc1ccc(-c2cnc(Nc3cnc(C#N)cn3)cc2NC[C@H]2CNCCO2)cc1] |
| 14 | 1137478-51-3 | Y-157 | 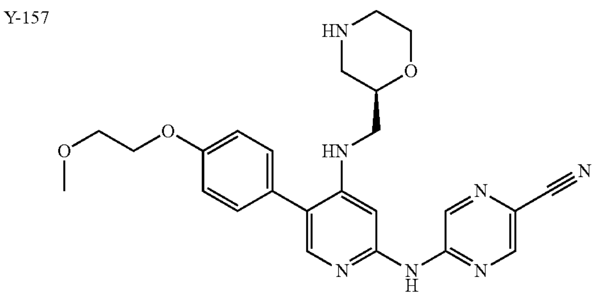 |
| 15 | 1137478-52-4 | Y-158 | 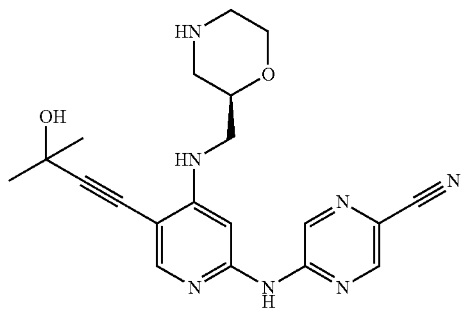 [SMILES: CC(C)(O)C#Cc1cnc(Nc2cnc(C#N)cn2)cc1NC[C@H]1CNCCO1] |
| 16 | 1137478-54-6 | Y-159 | 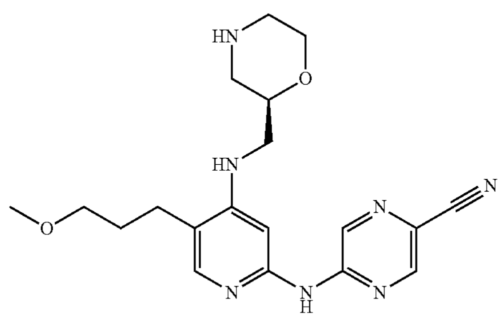 [SMILES: COCCCc1cnc(Nc2cnc(C#N)cn2)cc1NC[C@H]1CNCCO1] |

In the genus defined in Collins et al., 2009a, X may be —$CR^{45}$— (see, e.g., page 8, line 27 therein) and —$R^{45}$ may be -$Q^{45}$ (see, e.g., page 9, line 1 therein). The group -$Q^{45}$ is broadly defined (see, e.g., page 31, line 27 to page 38, line 13 therein), and may be, for example, —$CF_3$ (see, e.g., page 31, line 32 and page 33, line 21).

However, none of the examples in Collins et al., 2009a has X as —$CR^{45}$— with —$R^{45}$ as —$CF_3$.

Collins et al., 2009b, describes certain compounds of the following formula which inhibit Checkpoint Kinase 1 (CHK1) kinase function, and which are useful in the treatment of, e.g., cancer:

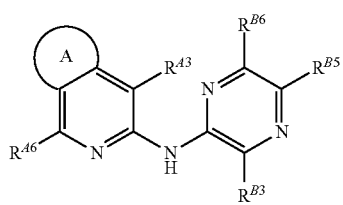

Walton et al., 2010, describes preclinical studies of the CHK1 inhibitor referred to as SAR-020106.

Almeida et al., 2008, describes certain pyrazolyl-amino-substituted pyrazines which allegedly are useful in the treatment of cancer.

Ioannidis et al., 2009, describes certain compounds which inhibit Janus-associated kinase (JAK). See, e.g., Scheme 5 on page 6526 therein.

Lin et al., 2005, describes certain macrocyclic urea compounds which allegedly are useful as protein kinase inhibitors. See, e.g., paragraph [0004] on page 1 therein.

Tao et al., 2005, describes certain macrocyclic urea compounds which allegedly are useful as protein kinase inhibitors. See, e.g., page 2 therein.

Li et al., 2007, describes the preparation and testing of certain macrocyclic urea CHK1 inhibitors. See, e.g., Table 1 on page 6502 therein.

Tao et al., 2007a, describes the preparation and testing of certain macrocyclic urea CHK1 inhibitors. See, e.g., Table 2 on page 6596 therein.

Tao et al., 2007b, describes the preparation and testing of certain macrocyclic urea CHK1 inhibitors. See, e.g., Table 3 on page 1517 therein.

One or more of the inventors have contributed to recent publications in which a number of CHK1 inhibitors are described, including the following compound, referred to as CCT244747. See, Lainchbury et al., 2012 (apparently published online on 19 Oct. 2012) and Walton et al., 2012 (apparently published 15 Oct. 2012).

CCT244747

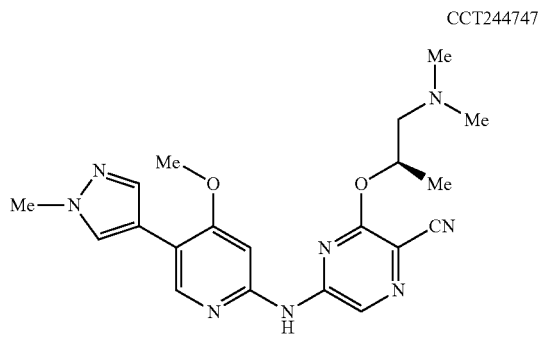 [SMILES: COc1cc(Nc2cnc(C#N)c(O[C@H](C)CN(C)C)n2)ncc1-c1cnn(C)c1]

SUMMARY OF THE INVENTION

One aspect of the invention pertains to 5-[[4-[[morpholin-2-yl]methylamino]-5-(trifluoromethyl)-2-pyridyl]amino] pyrazine-2-carbonitrile compounds (referred to herein as "TFM compounds") as described herein.

Another aspect of the invention pertains to a composition (e.g., a pharmaceutical composition) comprising a TFM compound, as described herein, and a pharmaceutically acceptable carrier or diluent.

In one embodiment, the composition (e.g., a pharmaceutical composition) is suitable for oral administration to a subject.

In one embodiment, the composition is in the form of an oral tablet, oral granules, an oral powder, an oral capsule, an oral cachet, or an oral pill.

Another aspect of the invention pertains to a method of preparing a composition (e.g., a pharmaceutical composition) comprising the step of mixing a TFM compound, as described herein, and a pharmaceutically acceptable carrier or diluent.

Another aspect of the present invention pertains to a method of inhibiting CHK1 kinase function in a cell, in vitro or in vivo, comprising contacting the cell with an effective amount of a TFM compound, as described herein.

In one embodiment, the method further comprises contacting the cell with one or more other agents selected from: (a) a DNA topoisomerase I or II inhibitor; (b) a DNA damaging agent; (c) an antimetabolite or a thymidylate synthase (TS) inhibitor; (d) a microtubule targeted agent; (e) ionising radiation; (f) an inhibitor of a mitosis regulator or a mitotic checkpoint regulator; (g) an inhibitor of a DNA damage signal transducer; and (h) an inhibitor of a DNA damage repair enzyme.

Another aspect of the present invention pertains to a method of regulating (e.g., inhibiting) cell proliferation (e.g., proliferation of a cell), inhibiting cell cycle progression, promoting cell apoptosis, or a combination of one or more these, in vitro or in vivo, comprising contacting a cell with an effective amount of a TFM compound, as described herein.

In one embodiment, the method further comprises contacting the cell with one or more other agents selected from: (a) a DNA topoisomerase I or II inhibitor; (b) a DNA damaging agent; (c) an antimetabolite or a thymidylate synthase (TS) inhibitor; (d) a microtubule targeted agent; (e) ionising radiation; (f) an inhibitor of a mitosis regulator or a mitotic checkpoint regulator; (g) an inhibitor of a DNA damage signal transducer; and (h) an inhibitor of a DNA damage repair enzyme.

Another aspect of the present invention pertains to a method of treatment comprising administering to a subject in need of treatment a therapeutically-effective amount of a TFM compound, as described herein, preferably in the form of a pharmaceutical composition.

In one embodiment, said administering is orally administering.

In one embodiment, the method further comprises administering to the subject one or more other agents selected from: (a) a DNA topoisomerase I or II inhibitor; (b) a DNA damaging agent; (c) an antimetabolite or a thymidylate synthase (TS) inhibitor; (d) a microtubule targeted agent; (e) ionising radiation; (f) an inhibitor of a mitosis regulator or a mitotic checkpoint regulator; (g) an inhibitor of a DNA damage signal transducer; and (h) an inhibitor of a DNA damage repair enzyme.

Another aspect of the present invention pertains to a TFM compound as described herein for use in a method of treatment of the human or animal body by therapy.

In one embodiment, the compound is for use in a method of treatment of the human or animal body by therapy by oral administration.

In one embodiment, the method of treatment comprises treatment with both (i) a TFM compound and (ii) one or more other agents selected from: (a) a DNA topoisomerase I or II inhibitor; (b) a DNA damaging agent; (c) an antimetabolite or a thymidylate synthase (TS) inhibitor; (d) a microtubule targeted agent; (e) ionising radiation; (f) an inhibitor of a mitosis regulator or a mitotic checkpoint regulator; (g) an inhibitor of a DNA damage signal transducer; and (h) an inhibitor of a DNA damage repair enzyme.

Another aspect of the present invention pertains to use of a TFM compound, as described herein, in the manufacture of a medicament for use in treatment.

In one embodiment, the medicament is a medicament for oral administration.

In one embodiment, the treatment comprises treatment with both (i) a medicament comprising a TFM compound and (ii) one or more other agents selected from: (a) a DNA topoisomerase I or II inhibitor; (b) a DNA damaging agent;

(c) an antimetabolite or a thymidylate synthase (TS) inhibitor; (d) a microtubule targeted agent; (e) ionising radiation; (f) an inhibitor of a mitosis regulator or a mitotic checkpoint regulator; (g) an inhibitor of a DNA damage signal transducer; and (h) an inhibitor of a DNA damage repair enzyme.

In one embodiment, the treatment is treatment of a disease or condition that is mediated by CHK1.

In one embodiment, the treatment is treatment of a disease or condition that is ameliorated by the inhibition of CHK1 kinase function.

In one embodiment, the treatment is treatment of a proliferative condition.

In one embodiment, the treatment is treatment of cancer.

In one embodiment, the treatment is treatment of head cancer; neck cancer; nervous system cancer; brain cancer; neuroblastoma; lung/mediastinum cancer; breast cancer; oesophagus cancer; stomach cancer; liver cancer; biliary tract cancer; pancreatic cancer; small bowel cancer; large bowel cancer; colorectal cancer; gynaecological cancer; genito-urinary cancer; ovarian cancer; thyroid gland cancer; adrenal gland cancer; skin cancer; melanoma; bone sarcoma; soft tissue sarcoma; paediatric malignancy; Hodgkin's disease; non-Hodgkin's lymphoma; myeloma; leukaemia; or metastasis from an unknown primary site.

In one embodiment, the treatment is treatment of: lung cancer, breast cancer, ovarian cancer, pancreatic cancer, colorectal cancer, lymphoma, melanoma, glioma, or neuroblastoma.

In one embodiment, the treatment is treatment of p53 deficient cancer.

In one embodiment, the treatment is treatment of MYC-amplified cancer.

In one embodiment, the treatment is treatment of c-MYC-amplified cancer.

In one embodiment, the treatment is treatment of MYCN-amplified cancer.

In one embodiment, the treatment is treatment of cancer characterised by overexpression of MYC.

In one embodiment, the treatment is treatment of cancer characterised by overexpression of MYCN.

In one embodiment, the treatment is treatment of cancer characterised by overexpression of c-MYC.

In one embodiment, the treatment is treatment of MYCN-amplified neuroblastoma.

In one embodiment, the treatment is treatment of c-MYC-amplified B cell lymphoma.

In one embodiment, the treatment is treatment of cancer characterised by increased endogenous replicative stress.

In one embodiment, the treatment is treatment of cancer characterised by increased endogenous activation of CHK1 signalling.

Another aspect of the present invention pertains to a kit comprising (a) a TFM compound, as described herein, preferably provided as a pharmaceutical composition and in a suitable container and/or with suitable packaging; and (b) instructions for use, for example, written instructions on how to administer the compound.

In one embodiment, the kit further comprises one or more other agents selected from: (a) a DNA topoisomerase I or II inhibitor; (b) a DNA damaging agent; (c) an antimetabolite or a thymidylate synthase (TS) inhibitor; (d) a microtubule targeted agent; (e) a systemic radiopharmaceutical; (f) an inhibitor of a mitosis regulator or a mitotic checkpoint regulator; (g) an inhibitor of a DNA damage signal transducer; and (h) an inhibitor of a DNA damage repair enzyme.

Another aspect of the present invention pertains to a TFM compound obtainable by a method of synthesis as described herein, or a method comprising a method of synthesis as described herein.

Another aspect of the present invention pertains to a TFM compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

One aspect of the present invention relates to compounds of the following formula, and pharmaceutically acceptable salts, hydrates, and solvates thereof (for convenience, collectively referred to herein as "5-[[4-[[morpholin-2-yl]methylamino]-5-(trifluoromethyl)-2-pyridyl]amino]pyrazine-2-carbonitrile compounds" or "TFA compounds"):

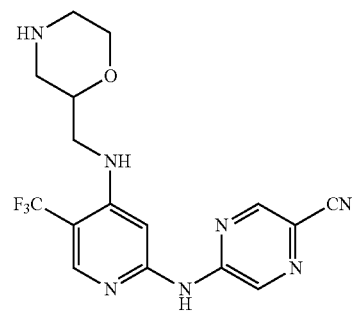

The point of attachment of the morpholinyl group is a chiral centre (marked by an asterisk in the following formula) which may independently be in the (R) or (S) configuration. Unless otherwise indicated, it is intended that both configurations are encompassed.

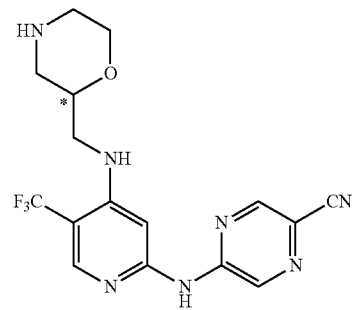

In one embodiment, the compound is a compound of the following formula, or a pharmaceutically acceptable salt, hydrate, or solvate thereof:

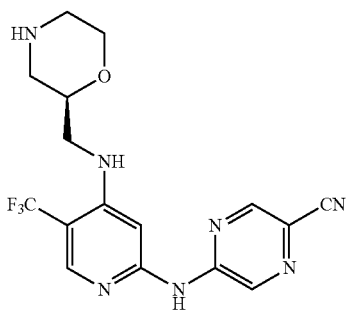 [SMILES: N#Cc1cnc(Nc2cc(NC[C@H]3CNCCO3)c(C(F)(F)F)cn2)cn1]

The above compound is also known as 5-[[4-[[(2R)-morpholin-2-yl]methylamino]-5-(trifluoromethyl)-2-pyridyl]amino]pyrazine-2-carbonitrile.

In one embodiment, the compound is a compound of the following formula, or a pharmaceutically acceptable salt, hydrate, or solvate thereof:

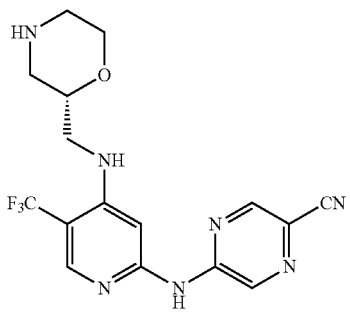 [SMILES: N#Cc1cnc(Nc2cc(NC[C@@H]3CNCCO3)c(C(F)(F)F)cn2)cn1]

The above compound is also known as 5-[[4-[[(2S)-morpholin-2-yl]methylamino]-5-(trifluoromethyl)-2-pyridyl]amino]pyrazine-2-carbonitrile.

Substantially Purified Forms

One aspect of the present invention pertains to TFM compounds, in purified form.

In one embodiment, the compound is in substantially purified form and/or in a form substantially free from contaminants.

In one embodiment, the compound is in a substantially purified form with a purity of least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of enantiomers, i.e., purified with respect to other compounds. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the compound is in a form substantially free from contaminants wherein the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than enantiomers. In one embodiment, the contaminants refer to other compounds and the other enantiomer.

In one embodiment, the compound is in a substantially purified form with an optical purity of at least 60% (i.e., 60% of the compound, on a molar basis, is the desired enantiomer, and 40% is undesired enantiomer), e.g., at least 70%, e.g., at least 80%, e.g., at least 90%, e.g., at least 95%, e.g., at least 97%, e.g., at least 98%, e.g., at least 99%.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

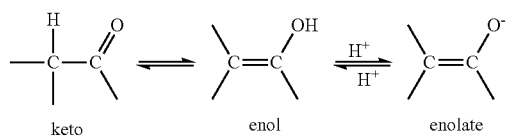

Note that specifically included in the term "isomers" are compounds with one or more isotopic substitutions. For example, H may be in any isotopic form, including $^1H$, $^2H$ (D), and $^3H$ (T); C may be in any isotopic form, including $^{13}C$, and $^{14}C$; O may be in any isotopic form, including $^{16}O$ and $^{18}O$; and the like.

Unless otherwise specified, a reference to a particular compound includes all such isomeric forms, including mixtures (e.g., racemic mixtures) thereof.

Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if a compound is anionic, or has a functional group which may be anionic (e.g., —COOH may be —COO⁻), then a salt may be formed with a suitable cation.

Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4$+). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If a compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, formic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Hydrates and Solvates

It may be convenient or desirable to prepare, purify, and/or handle a corresponding solvate of a compound. The term "solvate" is used herein in the conventional sense to refer to a complex of solute (e.g., compound, salt of compound) and solvent. If the solvent is water, the solvate may be conveniently referred to as a hydrate, for example, a hemi-hydrate, a mono-hydrate, a sesqui-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle a compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Greene and P. Wuts; 4th Edition; John Wiley and Sons, 2006).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH—Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH—Psec); or, in suitable cases (e.g., cyclic amines), as a nitroxide radical (>N—O•).

Prodrugs

It may be convenient or desirable to prepare, purify, and/or handle a compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

Compositions

One aspect of the present invention pertains to a composition (e.g., a pharmaceutical composition) comprising a TFM compound, as described herein, and a pharmaceutically acceptable carrier, diluent, or excipient.

Another aspect of the present invention pertains to a method of preparing a composition (e.g., a pharmaceutical composition) comprising mixing a TFM compound, as described herein, and a pharmaceutically acceptable carrier, diluent, or excipient.

In one preferred embodiment, the composition (e.g., a pharmaceutical composition) is suitable for oral administration to a subject.

In one preferred embodiment, the composition is in the form of an oral tablet, oral granules, an oral powder, an oral capsule, an oral cachet, or an oral pill.

Uses

The TFM compounds, as described herein, are useful, for example, in the treatment of disorders (e.g., diseases) that are ameliorated by the inhibition of CHK1 kinase function, as described herein.

Use in Methods of Inhibiting CHK1

One aspect of the present invention pertains to a method of inhibiting CHK1 kinase function, in vitro or in vivo, comprising contacting a CHK1 kinase with an effective amount of a TFM compound, as described herein.

One aspect of the present invention pertains to a method of inhibiting CHK1 kinase function in a cell, in vitro or in vivo, comprising contacting the cell with an effective amount of a TFM compound, as described herein.

In one embodiment, the method further comprises contacting the cell with one or more other agents selected from: (a) a DNA topoisomerase I or II inhibitor; (b) a DNA damaging agent; (c) an antimetabolite or a thymidylate synthase (TS) inhibitor; (d) a microtubule targeted agent; (e) ionising radiation; (f) an inhibitor of a mitosis regulator or a mitotic checkpoint regulator; (g) an inhibitor of a DNA damage signal transducer; and (h) an inhibitor of a DNA damage repair enzyme.

Suitable assays for determining CHK1 kinase function inhibition are described herein and/or are known in the art.

In one embodiment, the method is performed in vitro.

In one embodiment, the method is performed in vivo.

In one embodiment, the TFM compound is provided in the form of a pharmaceutically acceptable composition.

Any type of cell may be treated, including but not limited to, adipose, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound inhibits CHK1 kinase function. For example, suitable assays are described herein.

Use in Methods of Inhibiting Cell Proliferation, Etc.

The TFM compounds described herein, e.g., (a) regulate (e.g., inhibit) cell proliferation; (b) inhibit cell cycle progression; (c) promote cell apoptosis; or (d) a combination of one or more of these.

One aspect of the present invention pertains to a method of regulating (e.g., inhibiting) cell proliferation (e.g., proliferation of a cell), inhibiting cell cycle progression, promoting cell apoptosis, or a combination of one or more these, in vitro or in vivo, comprising contacting a cell with an effective amount of a TFM compound, as described herein.

In one embodiment, the method is a method of regulating (e.g., inhibiting) cell proliferation (e.g., proliferation of a cell), in vitro or in vivo, comprising contacting a cell with an effective amount of a TFM compound, as described herein.

In one embodiment, the method further comprises contacting the cell with one or more other agents selected from: (a) a DNA topoisomerase I or II inhibitor; (b) a DNA damaging agent; (c) an antimetabolite or a thymidylate synthase (TS) inhibitor; (d) a microtubule targeted agent; (e) ionising radiation; (f) an inhibitor of a mitosis regulator or a mitotic checkpoint regulator; (g) an inhibitor of a DNA damage signal transducer; and (h) an inhibitor of a DNA damage repair enzyme.

In one embodiment, the method is performed in vitro.

In one embodiment, the method is performed in vivo.

In one embodiment, the TFM compound is provided in the form of a pharmaceutically acceptable composition.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays which may conveniently be used to assess the activity offered by a particular compound are described herein.

For example, a sample of cells (e.g., from a tumour) may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to a TFM compound, as described herein, for use in a method of treatment of the human or animal body by therapy.

Another aspect of the present invention pertains to a TFM compound, as described herein, for use in a method of treatment of the human or animal body by therapy by oral administration.

In one embodiment, the method of treatment comprises treatment with both (i) a TFM compound, as described herein, and (ii) one or more other agents selected from: (a) a DNA topoisomerase I or II inhibitor; (b) a DNA damaging agent; (c) an antimetabolite or a thymidylate synthase (TS) inhibitor; (d) a microtubule targeted agent; (e) ionising radiation; (f) an inhibitor of a mitosis regulator or a mitotic checkpoint regulator; (g) an inhibitor of a DNA damage signal transducer; and (h) an inhibitor of a DNA damage repair enzyme.

Another aspect of the present invention pertains to (a) a DNA topoisomerase I or II inhibitor; (b) a DNA damaging agent; (c) an antimetabolite or a thymidylate synthase (TS) inhibitor; (d) a microtubule targeted agent; (e) a systemic radiopharmaceutical; (f) an inhibitor of a mitosis regulator or a mitotic checkpoint regulator; (g) an inhibitor of a DNA damage signal transducer; and (h) an inhibitor of a DNA damage repair enzyme, as described herein, for use in a method of treatment of the human or animal body by therapy, wherein the method of treatment comprises treatment with both (i) a TFM compound, as described herein, and (a) the DNA topoisomerase I or II inhibitor; (b) the DNA damaging agent; (c) the antimetabolite or the thymidylate synthase (TS) inhibitor; (d) the microtubule targeted agent; (e) the systemic radiopharmaceutical; (f) the inhibitor of a mitosis regulator or the mitotic checkpoint regulator; (g) the inhibitor of a DNA damage signal transducer; or (h) the inhibitor of a DNA damage repair enzyme.

Use in the Manufacture of Medicaments

Another aspect of the present invention pertains to use of a TFM compound, as described herein, in the manufacture of a medicament for use in treatment.

Another aspect of the present invention pertains to use of a TFM compound, as described herein, in the manufacture of a medicament for use in treatment by oral administration.

In one embodiment, the medicament comprises the TFM compound.

In one embodiment, the treatment comprises treatment with both (i) a medicament comprising a TFM compound, as described herein, and (ii) one or more other agents selected from: (a) a DNA topoisomerase I or II inhibitor; (b) a DNA damaging agent; (c) an antimetabolite or a thymidylate synthase (TS) inhibitor; (d) a microtubule targeted agent; (e) ionising radiation; (f) an inhibitor of a mitosis regulator or a mitotic checkpoint regulator; (g) an inhibitor of a DNA damage signal transducer; and (h) an inhibitor of a DNA damage repair enzyme.

Another aspect of the present invention pertains to use of (a) a DNA topoisomerase I or II inhibitor; (b) a DNA damaging agent; (c) an antimetabolite or a thymidylate synthase (TS) inhibitor; (d) a microtubule targeted agent; (e) ionising radiation; (f) an inhibitor of a mitosis regulator or a mitotic checkpoint regulator; (g) an inhibitor of a DNA damage signal transducer; or (h) an inhibitor of a DNA damage repair enzyme, as described herein, in the manufacture of a medicament for use in a treatment, wherein the treatment comprises treatment with both (i) a TFM compound, as described herein, and (a) the DNA topoisomerase I or II inhibitor; (b) the DNA damaging agent; (c) the antimetabolite or the thymidylate synthase (TS) inhibitor; (d) the microtubule targeted agent; (e) ionising radiation; (f) the inhibitor of a mitosis regulator or a mitotic checkpoint regulator; (g) the inhibitor of a DNA damage signal transducer; or (h) the inhibitor of a DNA damage repair enzyme Methods of Treatment Another aspect of the present invention pertains to a method of treatment comprising administering to a patient in need of treatment a therapeutically effective amount of a TFM compound, as described herein, preferably in the form of a pharmaceutical composition.

Another aspect of the present invention pertains to a method of treatment comprising orally administering to a patient in need of treatment a therapeutically effective amount of a TFM compound, as described herein, preferably in the form of a pharmaceutical composition.

In one embodiment, the method further comprises administering to the subject one or more other agents selected from: (a) a DNA topoisomerase I or II inhibitor; (b) a DNA damaging agent; (c) an antimetabolite or a thymidylate synthase (TS) inhibitor; (d) a microtubule targeted agent; (e) ionising radiation; (f) an inhibitor of a mitosis regulator or a mitotic checkpoint regulator; (g) an inhibitor of a DNA damage signal transducer; and (h) an inhibitor of a DNA damage repair enzyme.

Conditions Treated—Conditions Mediated by CHK1

In one embodiment (e.g., of use in methods of therapy, of use in the manufacture of medicaments, of methods of treatment), the treatment is treatment of a disease or condition that is mediated by CHK1.

Conditions Treated—Conditions Ameliorated by the Inhibition of CHK1 Kinase Function In one embodiment (e.g., of use in methods of therapy, of use in the manufacture of medicaments, of methods of treatment), the treatment is treatment of: a disease or condition that is ameliorated by the inhibition of CHK1 kinase function.

Disorders Treated—Proliferative Conditions

In one embodiment (e.g., of use in methods of therapy, of use in the manufacture of medicaments, of methods of treatment), the treatment is treatment of: a proliferative condition.

The term "proliferative condition," as used herein, pertains to an unwanted or uncontrolled cellular proliferation of excessive or abnormal cells which is undesired, such as neoplastic or hyperplastic growth.

In one embodiment, the treatment is treatment of: a proliferative condition characterised by benign, pre-malignant, or malignant cellular proliferation, including for example: neoplasms, hyperplasias, and tumours (e.g., histocytoma, glioma, astrocyoma, osteoma), cancers (see below), psoriasis, bone diseases, fibroproliferative disorders (e.g., of connective tissues), pulmonary fibrosis, atherosclerosis, smooth muscle cell proliferation in the blood vessels, such as stenosis or restenosis following angioplasty.

Disorders Treated—Cancer

In one embodiment (e.g., of use in methods of therapy, of use in the manufacture of medicaments, of methods of treatment), the treatment is treatment of cancer.

In one embodiment, the treatment is treatment of a proliferative condition.

In one embodiment, the treatment is treatment of cancer.

In one embodiment, the treatment is treatment of lung cancer, small cell lung cancer, non-small cell lung cancer, gastrointestinal cancer, stomach cancer, bowel cancer, colon cancer, rectal cancer, colorectal cancer, thyroid cancer, breast cancer, ovarian cancer, endometrial cancer, prostate cancer, testicular cancer, liver cancer, kidney cancer, renal cell carcinoma, bladder cancer, pancreatic cancer, brain cancer, neuroblastoma, glioma, sarcoma, osteosarcoma, bone cancer, nasopharyngeal cancer (e.g., head cancer, neck cancer), skin cancer, squamous cancer, Kaposi's sarcoma, melanoma, malignant melanoma, lymphoma, or leukemia.

In one embodiment, the treatment is treatment of:
- a carcinoma, for example a carcinoma of the bladder, breast, colon (e.g., colorectal carcinomas such as colon adenocarcinoma and colon adenoma), kidney, epidermal, liver, lung (e.g., adenocarcinoma, small cell lung cancer and non-small cell lung carcinomas), oesophagus, gall bladder, ovary, pancreas (e.g., exocrine pancreatic carcinoma), stomach, cervix, thyroid, prostate, skin (e.g., squamous cell carcinoma);
- a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma;
- a hematopoietic tumor of myeloid lineage, for example acute and chronic myelogenous leukemias, myelodysplastic syndrome, or promyelocytic leukemia;
- a tumour of mesenchymal origin, for example fibrosarcoma or habdomyosarcoma;
- a tumor of the central or peripheral nervous system, for example astrocytoma, neuroblastoma, glioma or schwannoma;
- melanoma; seminoma; teratocarcinoma; osteosarcoma; xenoderoma pigmentoum; keratoctanthoma; thyroid follicular cancer; or Kaposi's sarcoma.

In one embodiment, the treatment is treatment of head cancer; neck cancer; nervous system cancer; brain cancer; neuroblastoma; lung/mediastinum cancer; breast cancer; oesophagus cancer; stomach cancer; liver cancer; biliary tract cancer; pancreatic cancer; small bowel cancer; large bowel cancer; colorectal cancer; gynaecological cancer; genito-urinary cancer; ovarian cancer; thyroid gland cancer; adrenal gland cancer; skin cancer; melanoma; bone sarcoma; soft tissue sarcoma; paediatric malignancy; Hodgkin's disease; non-Hodgkin's lymphoma; myeloma; leukaemia; or metastasis from an unknown primary site.

In one embodiment, the treatment is treatment of: lung cancer, breast cancer, ovarian cancer, pancreatic cancer, colorectal cancer, lymphoma, melanoma, glioma, or neuroblastoma.

In one embodiment, the cancer is characterised by, or further characterised by, being p53 deficient cancer. In one embodiment, the cancer is p53 deficient cancer.

In one embodiment, the cancer is characterised by, or further characterised by, being MYC-amplified cancer. In one embodiment, the cancer is MYC-amplified cancer.

In one embodiment, the cancer is characterised by, or further characterised by, being c-MYC-amplified cancer. In one embodiment, the cancer is c-MYC-amplified cancer.

In one embodiment, the cancer is characterised by, or further characterised by, being MYCN-amplified cancer. In one embodiment, the cancer is MYCN-amplified cancer.

In one embodiment, the cancer is characterised by, or further characterised by, overexpression of MYC. In one embodiment, the cancer is cancer characterised by overexpression of MYC.

In one embodiment, the cancer is characterised by, or further characterised by, overexpression of MYCN. In one embodiment, the cancer is cancer characterised by overexpression of MYCN.

In one embodiment, the cancer is characterised by, or further characterised by, overexpression of c-MYC. In one embodiment, the cancer is cancer characterised by overexpression of c-MYC.

In one embodiment, the cancer is MYCN-amplified neuroblastoma.

In one embodiment, the cancer is c-MYC-amplified B cell lymphoma.

In one embodiment, the cancer is characterised by, or further characterised by, increased endogenous replicative stress. In one embodiment, the cancer is cancer characterised by increased endogenous replicative stress.

In one embodiment, the cancer is characterised by, or further characterised by, increased endogenous activation of CHK1 signalling. In one embodiment, the cancer is cancer characterised by increased endogenous activation of CHK1 signalling.

In one embodiment, the treatment is treatment of cancer metastasis.

In one embodiment, the cancer is characterised by, or further characterised by, cancer stem cells.

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of cell migration (the spread of cancer cells to other parts of the body), the inhibition of invasion (the spread of tumour cells into neighbouring normal structures), or the promotion of cell apoptosis (programmed cell death). The compounds of the present invention may be used in the treatment of the cancers described herein, independent of the mechanisms discussed herein.

Treatment

The term "treatment," as used herein in the context of treating a disorder, pertains generally to treatment of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

One aspect of the present invention pertains to a compound as described herein, in combination with one or more (e.g., 1, 2, 3, 4, etc.) additional therapeutic agents, for example, agents or therapies that regulate cell growth or survival or differentiation via a different mechanism, thus treating several characteristic features of cancer development.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Additional Agents for Combination Therapy

As discussed herein, in some embodiments, the TFM compound is employed in combination with (e.g., in conjunction with) with one or more other agents selected from: (a) a DNA topoisomerase I or II inhibitor; (b) a DNA damaging agent; (c) an antimetabolite or a thymidylate synthase (TS) inhibitor; (d) a microtubule targeted agent; (e) ionising radiation; (f) an inhibitor of a mitosis regulator or a mitotic checkpoint regulator; (g) an inhibitor of a DNA damage signal transducer; and (h) an inhibitor of a DNA damage repair enzyme.

When both a TFM compound and one or more other agents are employed, they may be used (e.g., contacted, administered, etc.) in any order. Furthermore, they may be used (e.g., contacted, administered, etc.) together, as part of a single formulation, or separately, as separate formulations.

For example, in regard to methods of treatment employing both a TFM compound and one or more other agents, treatment with (e.g., administration of) the TFM compound may be prior to, concurrent with, or may follow, treatment with (e.g., administration of) the one or more other agents, or a combination thereof.

In one embodiment, treatment with (e.g., administration of) a TFM compound is concurrent with, or follows, treatment with (e.g., administration of) the one or more other agents.

In one embodiment, the one or more other agents is a DNA topoisomerase I or II inhibitor; for example, Etoposide, Topotecan, Camptothecin, Irinotecan, SN-38, Doxorubicin, Daunorubicin, Epirubicin, and Mitoxantrone.

In one embodiment, the one or more other agents is a DNA damaging agent; for example, an alkylating agent, for example, Temozolomide, Dacarbazine, Mitomycin C, Cyclophosphamide, Ifosfamide, BCNU, CCNU, Melphalan, Busulfan, and Chlorambucil; a platinating agent, for example, Cisplatin, Carboplatin, and Oxaliplatin; or a compound that generates free radicals, for example, Bleomycin.

In one embodiment, the one or more other agents is an antimetabolite or a thymidylate synthase (TS) inhibitor; for example, 5-Fluorouracil, Hydroxyurea, Gemcitabine, Cytarabine, Fludarabine, Capecitabine, Nelarabine, Raltitrexed, Pemetrexed and ZD9331.

In one embodiment, the one or more other agents is a microtubule targeted agent; for example, Paclitaxel, Docetaxel, Cabazitaxel, Eribulin, Vincristine, Vinblastine, and Vinorelbine.

In one embodiment, the one or more other agents is ionising radiation (e.g., as part of radiotherapy), for example, delivered by external beam irradiation or delivered by administration of systemic radiopharmaceuticals, for example, $^{131}$I-Metaiodobenzylguanidine, Sodium ($^{131}$I) Iodide, Iodine ($^{131}$I) Tositumab, and Ibritumomab ($^{90}$Y) Tiuxetan.

In one embodiment, the one or more other agents is an inhibitor of a mitosis regulator or a mitotic checkpoint regulator, for example, an inhibitor of Wee1 kinase, an inhibitor of Aurora kinase, or an inhibitor of polo-like kinase 1.

In one embodiment, the one or more other agents is an inhibitor of a DNA damage signal transducer, for example, an inhibitor of ATR kinase, an inhibitor of ATM kinase, an inhibitor of CHK2, or an inhibitor of MK2.

In one embodiment, the one or more other agents is an inhibitor of a DNA damage repair enzyme, for example, an inhibitor of poly ADP ribose polymerase (PARP), for example, Olaparib.

Other Uses

The TFM compounds described herein may also be used as cell culture additives to inhibit CHK1 kinase function, e.g., to inhibit cell proliferation, etc.

The TFM compounds described herein may also be used as part of an in vitro assay, for example, in order to determine whether a candidate host is likely to benefit from treatment with the compound in question.

The TFM compounds described herein may also be used as a standard, for example, in an assay, in order to identify other compounds, other CHK1 kinase function inhibitors, other anti-proliferative agents, other anti-cancer agents, etc.

Kits

One aspect of the invention pertains to a kit comprising (a) a TFM compound as described herein, or a composition comprising a TFM compound as described herein, e.g., preferably provided in a suitable container and/or with suitable packaging; and (b) instructions for use, e.g., written instructions on how to administer the compound or composition.

In one embodiment, the kit further comprises one or more other agents selected from: (a) a DNA topoisomerase I or II inhibitor; (b) a DNA damaging agent; (c) an antimetabolite or a thymidylate synthase (TS) inhibitor; (d) a microtubule targeted agent; (e) a systemic radiopharmaceutical; (f) an inhibitor of a mitosis regulator or a mitotic checkpoint regulator; (g) an inhibitor of a DNA damage signal transducer; and (h) an inhibitor of a DNA damage repair enzyme.

The written instructions may also include a list of indications for which the active ingredient is a suitable treatment.

Routes of Administration

The TFM compound or pharmaceutical composition comprising the TFM compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Preferably, the route of administration is oral, and the TFM compound or pharmaceutical composition comprising the TFM compound is administered to a subject orally.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for a TFM compound to be administered alone, it is preferable to present it as a pharmaceutical formulation (e.g., composition, preparation, medicament) comprising at least one TFM compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising mixing at least one TFM compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additionally contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 10 μg/m L, for example from about 10 ng/mL to about 1 μg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the TFM compounds, and compositions comprising the TFM compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular TFM compound, the route of administration, the time of administration, the rate of excretion of the TFM compound, the duration of the treatment, other drugs, compounds, and/or materials used in combination, the severity of the disorder, and the species, sex, age, weight, condition, general health, and prior medical history of the patient. The amount of TFM compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the TFM compound is in the range of about 10 μg to about 250 mg (more typically about 100 μg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

Chemical Synthesis

The following examples are provided solely to illustrate the present invention and are not intended to limit the scope of the invention, as described herein.

Synthesis 1

5-[[4-[[(2R)-morpholin-2-yl]methylamino]-5-(trifluoromethyl)-2-pyridyl]amino]pyrazine-2-carbonitrile (Compound 1)

Synthesis 1A (R)-tert-Butyl 2-(tosyloxymethyl)morpholine-4-carboxylate

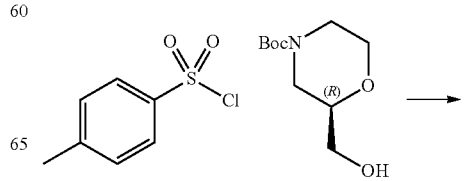

31
-continued

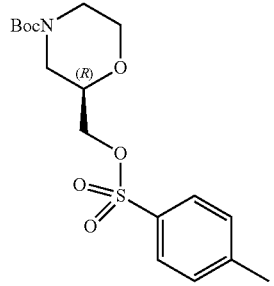

Triethylamine (15.46 mL, 110 mmol) was added to (R)-tert-butyl 2-(hydroxymethyl)-morpholine-4-carboxylate (21.73 g, 100 mmol) in dichloromethane (50.0 mL) to give a colorless solution which was cooled with an ice bath. 4-Toluenesulfonyl chloride (20.02 g, 105 mmol) was added in small portions with the internal temperature maintained below 3° C. The slurry was stirred for 21 hours at room temperature before concentrating in vacuo. The crude material was dissolved in ethyl acetate (750 mL), washed with water (450 mL), brine (200 mL) and dried over magnesium sulfate. After filtration and removal of the volatiles in vacuo, hexane (150 mL) was added and the resulting white precipitate was filtered, washed with hexane (300 mL), and dried to give the title compound as a white powder (35.66 g, 96%).

$^1$H NMR (500 MHz, CDCl$_3$) δ 1.46 (9H, s), 2.46 (3H, s), 2.62-2.73 (1H, m), 2.85-2.94 (1H, m), 3.44-3.49 (1H, m), 3.58-3.63 (1H, m), 3.77-3.94 (3H, m), 3.99-4.06 (2H, m), 7.36 (2H, d, J=8.5 Hz), 7.80 (2H, d, J=8.5 Hz). LC-MS (Agilent 4 min) R$_t$ 2.90 min; m/z (ESI) 372 [M+H$^+$].

Synthesis 1B (S)-tert-Butyl 2-((2-chloro-5-(trifluoromethyl)pyridin-4-ylamino)methyl)morpholine-4-carboxylate 32
-continued To a solution of 2-chloro-5-(trifluoromethyl)pyridin-4-amine (2.9 g, 14.75 mmol) in dimethylformamide (95 mL) was added sodium hydride (60% by wt in oil; 1.180 g, 29.5 mmol) portionwise at room temperature and the mixture was stirred for 10 minutes at 80° C. (R)-tert-Butyl 2-(tosyloxymethyl)morpholine-4-carboxylate was added portionwise and the reaction mixture was stirred at 80° C. for 2.5 hours. The reaction mixture was cooled and poured into saturated aqueous sodium hydrogencarbonate solution (100 mL), diluted with water (250 mL) and extracted with ethyl acetate (100 mL). After separating the two layers, the aqueous layer was further extracted with ethyl acetate (2×100 mL). The combined organic layers were washed with brine (4×100 mL), dried over magnesium sulfate, filtered, concentrated and thoroughly dried under vacuum. The crude material was purified by column chromatography, eluting initially with 2.5% diethyl ether/2.5% ethyl acetate in dichloromethane, and then with 20% diethyl ether in dichloromethane as the desired product eluted from the column. The appropriate fractions were combined and concentrated to give the title compound as an off-white powder (4.51 g, 77%).

$^1$H NMR (500 MHz, CDCl$_3$) δ 1.49 (9H, s), 2.70-2.84 (1H, m), 2.92-3.05 (1H, m), 3.18-3.23 (1H, m), 3.33-3.37 (1H, m), 3.55-3.61 (1H, m), 3.66-3.71 (1H, m), 3.80-4.07 (3H, m), 5.32 (1H, broad s), 6.61 (1H, s), 8.24 (1H, s). LC-MS (Agilent 4 min) R$_t$ 3.04 min; m/z (ESI) 396 [MH$^+$].

Synthesis 10

(S)-tert-Butyl 2-((2-(5-cyanopyrazin-2-ylamino)-5-(trifluoromethyl)pyridin-4-ylamino)methyl)morpholine-4-carboxylate

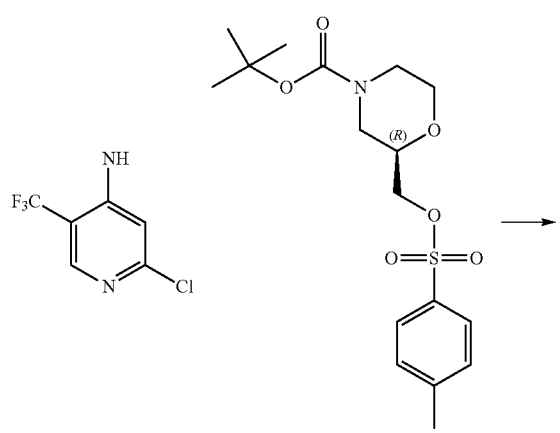

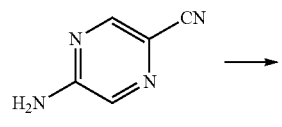

33

-continued

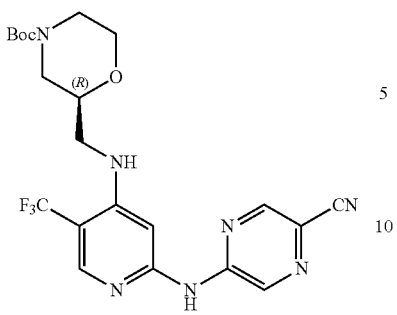

(S)-tert-Butyl 2-((2-chloro-5-(trifluoromethyl)pyridin-4-ylamino)methyl)morpholine-4-carboxylate (4.67 g, 11.8 mmol), 2-amino-5-cyanopyrazine (1.98 g, 16.5 mmol), tris(dibenzylideneacetone)dipalladium(0) (0.86 g, 0.94 mmol), rac-2,2'-bis(diphenylphosphino)-1,1'-binaphthyl (0.54 g, 0.87 mmol) and caesium carbonate (7.69 g, 23.6 mmol) were suspended in anhydrous dioxane (108 mL) under argon. Argon was bubbled through the mixture for 30 minutes, after which the suspension was heated to 100° C. for 29 hours. The reaction mixture was cooled and diluted with dichloromethane, then absorbed onto silica gel. The pre-absorbed silica gel was added to a 340 g KP-Sil SNAP column which had been equilibrated with 20% ethyl acetate in hexane. Column chromatography, eluting with a gradient of 20-35% ethyl acetate in hexane, gave partially purified material as an orange gum. This was further purified by column chromatography, eluting with 20% ethyl acetate in dichloromethane, to give the title compound as a light tan powder (3.28 g, 58%).

$^1$H NMR (500 MHz, CDCl$_3$) δ 1.49 (9H, s), 2.73-2.86 (1H, m), 2.94-3.07 (1H, m), 3.26-3.31 (1H, m), 3.38-3.43 (1H, m), 3.57-3.61 (1H, m), 3.70-3.75 (1H, m), 3.83-4.08 (3H, m), 5.31 (1H, broad s), 7.12 (1H, s), 8.13 (1H, s), 8.23 (1H, s), 8.57 (1H, s), 8.87 (1H, s). LC-MS (Agilent 4 min) R$_t$ 2.90 min; m/z (ESI) 480 [MH$^+$].

Synthesis 1D

5-[[4-[[(2R)-Morpholin-2-yl]methylamino]-5-(trifluoromethyl)-2-pyridyl]amino]pyrazine-2-carbonitrile (Compound 1)

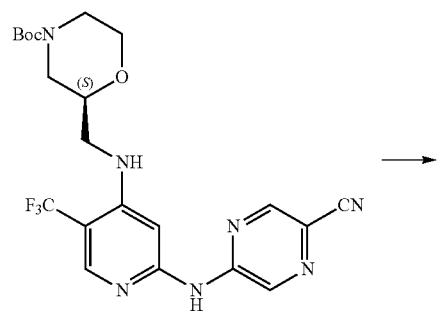

34

-continued

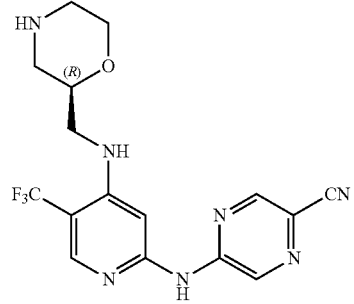 [SMILES: N#Cc1cnc(Nc2cc(NC[C@H]3CNCCO3)c(C(F)(F)F)cn2)cn1]

A solution of (S)-tert-butyl 2-((2-(5-cyanopyrazin-2-ylamino)-5-(trifluoromethyl)pyridin-4-ylamino)methyl)morpholine-4-carboxylate (1.09 g, 2.273 mmol) in dichloromethane (8 mL) was added dropwise over 10 minutes to a solution of trifluoroacetic acid (52.7 mL, 709 mmol) and triisopropylsilane (2.61 mL, 12.73 mmol) in dry dichloromethane (227 mL) at room temperature. After stirring for 30 minutes, the mixture was concentrated in vacuo. The concentrate was resuspended in dichloromethane (200 mL) and concentrated in vacuo, then resuspended in toluene (100 mL) and concentrated.

The above procedure was performed in triplicate (starting each time with 1.09 g (S)-tert-butyl 2-((2-(5-cyanopyrazin-2-ylamino)-5-(trifluoromethyl)pyridin-4-ylamino)methyl)morpholine-4-carboxylate) and the three portions of crude product so generated were combined for purification by ion exchange chromatography on 2×20 g Biotage NH2 Isolute columns, eluting with methanol. The eluant was concentrated and 10% methanol in diethyl ether (25 mL) was added. The resulting solid was filtered, washed with diethyl ether (30 mL), and dried in vacuo to give the title compound as a light straw coloured powder (2.30 g, 89%).

$^1$H NMR (500 MHz, CD$_3$OD) δ 2.62 (1H, J=12, 10 Hz), 2.78-2.84 (2H, m), 2.95 (1H, dd, J=12, 2 Hz), 3.27-3.38 (2H, m), 3.63 (1H, ddd, J=14, 9.5, 3 Hz), 3.73-3.78 (1H, m), 3.91 (1H, ddd, J=11, 4, 2 Hz), 7.26 (1H, s), 8.18 (1H, s), 8.63 (1H, s), 9.01 (1H, s). LC-MS (Agilent 4 min) R$_t$ 1.22 min; m/z (ESI) 380 [M+H$^+$]. Optical rotation $[α]_D^{24}$=+7.0 (c 1.0, DMF).

Synthesis 2

5-[[4-[[(2S)-Morpholin-2-yl]methylamino]-5-(trifluoromethyl)-2-pyridyl]amino]pyrazine-2-carbonitrile (Compound 2)

Synthesis 2A (S)-tert-Butyl 2-(tosyloxymethyl)morpholine-4-carboxylate

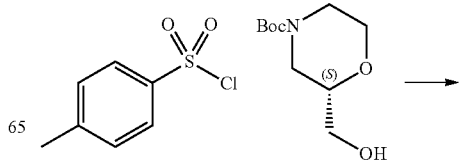

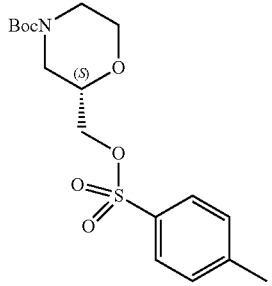

Triethylamine (6.05 mL, 43.0 mmol) was added to (S)-tert-butyl 2-(hydroxymethyl)-morpholine-4-carboxylate (8.5 g, 39.1 mmol) in dichloromethane (19.56 mL) to give a colourless solution. 4-Toluenesulfonyl chloride (7.83 g, 41.1 mmol) was added in small portions at 0° C. The reaction was stirred for 18 hours at room temperature, after which it was concentrated by evaporation under reduced pressure. The concentrate was dissolved in ethyl acetate (300 mL) and the resulting solution was washed with water (150 mL), brine (150 mL), dried over magnesium sulphate, filtered and concentrated by evaporation under reduced pressure. Hexane was added to the concentrate and the volatiles were removed under vacuum to give the title compound as a white powder (14.46 g, 99%).

$^1$H NMR (500 MHz, CDCl$_3$) δ 1.46 (9H, s), 2.46 (3H, s), 2.61-2.75 (1H, m), 2.85-2.94 (1H, m), 3.43-3.49 (1H, m), 3.58-3.63 (1H, m), 3.76-3.93 (3H, m), 3.99-4.06 (2H, m), 7.35 (2H, d, J=8.5 Hz), 7.80 (2H, d, J=8.5 Hz). LC-MS (Agilent 4 min) R$_t$ 2.94 min; m/z (ESI) 394 [M+Na$^+$].

Synthesis 2B (R)-tert-Butyl 2-((2-chloro-5-(trifluoromethyl)pyridin-4-ylamino)methyl)morpholine-4-carboxylate

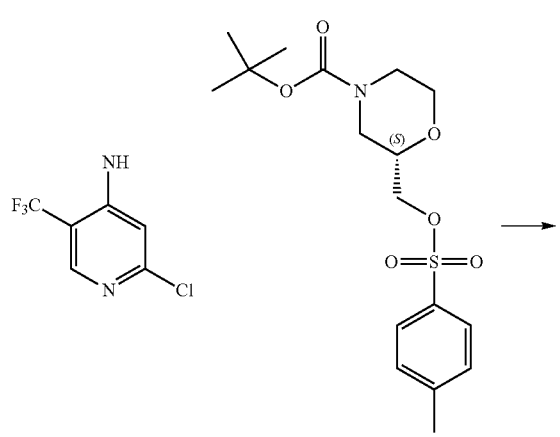

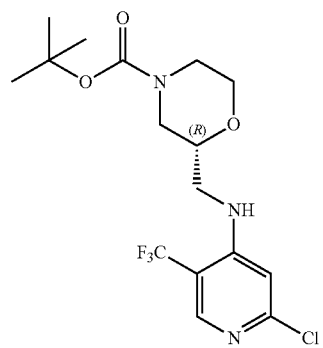

To a solution of 2-chloro-5-(trifluoromethyl)pyridin-4-amine (1 g, 5.09 mmol) in dimethylformamide (32.6 mL) was added sodium hydride (60% by wt in oil; 0.407 g, 10.18 mmol) portionwise at room temperature followed by stirring for 10 minutes at 80° C. (S)-tert-Butyl 2-(tosyloxymethyl)morpholine-4-carboxylate (2.268 g, 6.11 mmol) was then added portionwise and the reaction mixture was stirred at 80° C. for 2.5 hours. After cooling, the mixture was partitioned between saturated aqueous sodium hydrogencarbonate solution (30 mL), water (100 mL) and ethyl acetate (30 mL). The organic layer was separated and the aqueous layer was further extracted with ethyl acetate (2×30 mL). The combined organic layers were washed with brine (2×70 mL), dried over magnesium sulfate, filtered, concentrated and dried thoroughly in vacuo. The crude material was purified by column chromatography on a 90 g Thomson SingleStep column, eluting with an isocratic mix of 2.5% diethyl ether/2.5% ethyl acetate in dichloromethane, to give the title compound as a clear gum that later crystallised to give a white powder (1.47 g, 73%).

$^1$H NMR (500 MHz, CDCl$_3$) δ 1.48 (9H, s), 2.71-2.83 (1H, m), 2.92-3.05 (1H, m), 3.18-3.23 (1H, m), 3.33-3.37 (1H, m), 3.56-3.61 (1H, m), 3.66-3.71 (1H, m), 3.80-4.07 (3H, m), 5.32 (1H, broad s), 6.61 (1H, s), 8.24 (1H, s). LC-MS (Agilent 4 min) R$_t$ 3.04 min; m/z (ESI) 396 [MH$^+$].

Synthesis 2C (R)-tert-Butyl 2-((2-(5-cyanopyrazin-2-ylamino)-5-(trifluoromethyl)pyridin-4-ylamino)methyl)morpholine-4-carboxylate

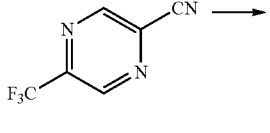

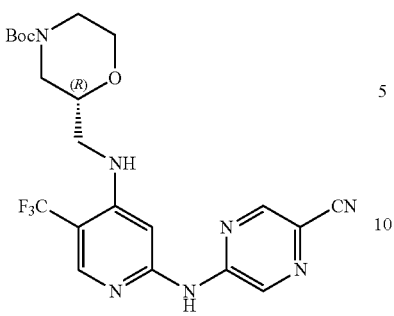

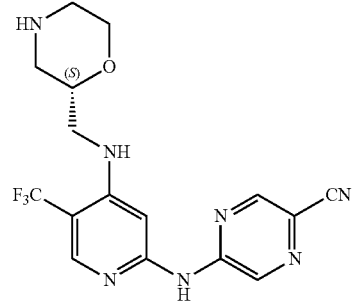 [SMILES: N#Cc1cnc(Nc2cc(NC[C@@H]3CNCCO3)c(C(F)(F)F)cn2)cn1]

(R)-tert-Butyl 2-((2-chloro-5-(trifluoromethyl)pyridin-4-ylamino)methyl)morpholine-4-carboxylate (1.44 g, 3.64 mmol), 2-amino-5-cyanopyrazine (0.612 g, 5.09 mmol, 1.4 eq.), tris(dibenzylideneacetone)dipalladium(0) (0.267 g, 0.291 mmol, 0.08 eq.), rac-2,2'-bis(diphenylphosphino)-1,1'-binaphthyl (0.362 g, 0.582 mmol, 0.16 eq.) and caesium carbonate (2.37 g, 7.28 mmol) were suspended in anhydrous dioxane (33 mL) under argon. Argon was bubbled through the mixture for 30 minutes, after which the mixture was heated to 100° C. for 22 hours. The reaction mixture was cooled and diluted with dichloromethane, then absorbed on to silica gel. The pre-absorbed silica gel was added to a 100 g KP-Sil SNAP column which was eluted with 20-50% ethyl acetate in hexanes to give the partially purified product as an orange gum. The crude product was dissolved in dichloromethane and purified by column chromatography on a 90 g SingleStep Thomson column, eluting with 20% ethyl acetate in dichloromethane, to give the title compound (1.19 g, 68%).

$^1$H NMR (500 MHz, CDCl$_3$) δ 1.50 (9H, s), 2.71-2.88 (1H, m), 2.93-3.08 (1H, m), 3.27-3.32 (1H, m), 3.40-3.44 (1H, m), 3.55-3.64 (1H, m), 3.71-3.77 (1H, m), 3.82-4.11 (3H, m), 5.33 (1H, broad s), 7.19 (1H, s), 8.23 (1H, s), 8.58 (1H, s), 8.84 (1H, s). LC-MS (Agilent 4 min) R$_t$ 2.93 min; m/z (ESI) 480 [MH$^+$].

Synthesis 2D

5-[[4-[[(2S)-Morpholin-2-yl]methylamino]-5-(trifluoromethyl)-2-pyridyl]amino]pyrazine-2-carbonitrile (Compound 2)

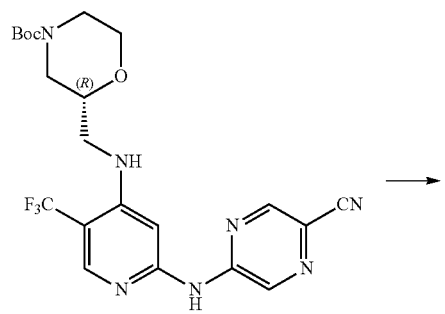

A solution of (R)-tert-butyl 2-((2-(5-cyanopyrazin-2-ylamino)-5-(trifluoromethyl)pyridin-4-ylamino)methyl)morpholine-4-carboxylate (1.19 g, 2.48 mmol) in dichloromethane (8 mL) was added dropwise over 10 minutes to a solution of trifluoroacetic acid (57.5 mL, 774 mmol) and triisopropylsilane (2.85 mL, 13.90 mmol) in dry dichloromethane (248 mL) at room temperature. After stirring for 30 minutes, the mixture was concentrated in vacuo. The concentrate was resuspended in dichloromethane (200 mL) and concentrated in vacuo, then resuspended in toluene (100 mL) and concentrated in vacuo. The crude material was purified by ion exchange chromatography on a 20 g Biotage NH2 Isolute column, eluting with methanol. The eluant was concentrated and 10% methanol in diethyl ether (8 mL) was added. The solid was filtered, washed with diethyl ether (20 mL), and dried in vacuo to give the title compound as a light straw coloured powder (0.604 g, 64% yield).

$^1$H NMR (500 MHz, CD$_3$OD) δ 2.62 (1H, J=12, 10 Hz), 2.78-2.84 (2H, m), 2.95 (1H, dd, J=12, 2 Hz), 3.27-3.38 (2H, m), 3.63 (1H, ddd, J=14, 9.5, 3 Hz), 3.73-3.78 (1H, m), 3.91 (1H, ddd, J=11, 4, 2 Hz), 7.26 (1H, s), 8.18 (1H, s), 8.63 (1H, s), 9.01 (1H, s). LC-MS (Agilent 4 min) R$_t$ 1.26 min; m/z (ESI) 380 [M+H$^+$]. Optical rotation [α]$_D^{24}$=−6.9 (c 1.0, DMF).

Biological Methods

Assay 1: Determination of Inhibitor Potency Vs. CHK1 in Caliper Assay Format

CHK1 kinase activity was measured in a microfluidic assay that monitors the separation of a phosphorylated product from its substrate. The assay was run on an EZ Reader II (Caliper Life Sciences Ltd, Runcorn, UK) using separation buffer (#760367 Caliper LS) containing CR-8 (500 nM, #760278, Caliper LS). An ECHO® 550 (Labcyte Inc™) acoustic dispenser was used to generate duplicate 8 pt dilution curves directly into 384 polypropylene assay plates (Greiner Bio-One, Gloucestershire, UK). For each test compound a 50 µM stock concentration in 100% DMSO was used. The total amount of DMSO dispensed per well was 250 nL to give a final assay concentration of 2.5% DMSO and test compound concentrations in the range 0.5-1000 nM. To this assay plate, 6 µL CHK1 (2 nM final concentration, in-house protein preparation), 2 peptide 10 (5-FAM-KKK-VSRSGLYRSPSMPENLNRPR—COOH (SEQ ID NO: 1), 1.5 µM final concentration, #760354 Caliper LS) and 2 µL ATP (90 µM final concentration) all diluted in kinase buffer (HEPES 50 mM, NaN3 0.02%, BSA 0.01%, sodium orthovanadate 0.1 mM, DTT 1 mM, MgCl2 2 mM, Tween 20 0.1%) were added. The plate was sealed and centrifuged (1 minute, 1000 rpm) before incubation for one hour at room temperature. The reaction was stopped by the addition of separation buffer (90 The plate was read on an EZ Reader II, using a 12-sipper chip (760137-0372R, Caliper LS) with instrument settings of 1.5 psi and 1750 ΔV. The percentage conversion of product from substrate was generated automatically and the percentage inhibition was calculated relative to blank wells (containing no enzyme and 2.5% DMSO) and total wells (containing all reagents and 2.5% DMSO). CHK1 IC50 values were calculated in GraphPad Prism5 using a non linear regression fit of the log (inhibitor concentration) vs. response with variable slope equation.

Assay 2: Cellular Potency in Mitosis Inhibition Assay (MIA)

Checkpoint abrogation by CHK1 kinase function inhibitors in combination with genotoxic agents was assessed using a europium based ELISA assay designed to quantify the number of cells trapped in mitosis after treatment with a genotoxic agent (to induce G2 arrest) followed by a CHK1 inhibitor test compound in combination with nocodazole to abrogate this arrest. HT29 cells were seeded at $10^4$ cells per well into 96-well plates in a volume of 160 µL and left to attach for 36 hours. Etoposide (10 mM stock in DMSO) was diluted in medium to 250 µM and then 40 µL was added to appropriate wells to give a final concentration of 50 µM and incubated for 1 hour. This treatment had previously been optimised to induce a G2 arrest in 80% of cells 16 hours following treatment. After genotoxic drug exposure, the medium was removed and replaced with fresh medium (160 µL). Cells were either untreated (untreated control or etoposide pre-treatment alone), exposed to nocodazole following etoposide pre treatment or nocodazole alone (100 ng/mL final concentration), or exposed to increasing concentrations of test compound (from 0.01 nM to 200 µM final concentration) in combination with nocodazole (100 ng/mL final concentration). CHK1 inhibitor test compounds were added in 40 µL aliquots using quadruplicate wells for each concentration. After 21 hours exposure, the medium was removed and cells were fixed in 4% formaldehyde in phosphate buffered saline (PBS, pH 7.4, pre-cooled to 4° C.) for 30 minutes at 4° C., followed by 100% methanol (pre-cooled to −20° C.) for 10 minutes at ambient temperature. Wells were washed with PBS and blocked with 5% dried milk (Marvel) in Tris-buffered saline (TBS, pH 7.4) at 37° C. for 30 minutes. Each well was washed three times with water containing 0.1% Tween 20. Primary antibody (MPM-2, Upstate cat#05-368, 1 µg/mL in 5% milk in TBS) was added to each well and incubated overnight with shaking at 4° C. Primary antibody was removed and wells were washed with water containing 0.1% Tween 20. The secondary antibody (europium labelled anti-mouse, Perkin-Elmer cat# AD0124, 333 ng/mL in assay buffer Perkin-Elmer cat#1244-111) was added to each well and incubated at 37° C. for 1 hour. Each well was washed with water 0.1% containing Tween 20 and treated with enhancement solution (Perkin-Elmer cat#1244-105). Europium emissions were counted on a Wallac, Victor2 counter (Perkin-Elmer, Bucks UK). Appropriate controls were included and results were expressed as the concentration of CHK1 inhibitor test compound required to allow 50% of cells to enter mitosis (MIA $IC_{50}$).

Assay 3: Assessment of Selectivity in Cells for CHK1-Dependent Checkpoint Abrogation Versus Cytotoxicity Compound cytotoxicity was assessed using a 96 hour sulforhodamine B assay (SRB, Sigma catalog number S9012). HT29 or SW620 cells were seeded at 1.6 to $3.2 \times 10^3$ cells per well in 96-well plates in a volume of 160 µL medium and allowed to attach for 36 hours prior to treatment. For cytotoxicity assays of CHK1 inhibitors (10 mM stock in DMSO) the compounds were serially diluted in medium from a starting concentration of 250 µM and then 40 µL was added to appropriate wells in quadruplicate to give a final concentration range of 50 to 0.1 µM (10 concentrations). For genotoxic agents, the compounds (SN38, LKT laboratories catalog number C0154 and gemcitabine, Lilly "Gemzar", 10 mM stock in DMSO) were serially diluted in medium from a starting concentration of 2 µM and 40 µL was added to each well in quadruplicate to give final concentrations from 200 to 0.39 nM (10 concentrations). Cells were incubated for 96 hours (four doublings) at 37° C. in a humidified 5% $CO_2$ environment and then fixed and stained with SRB. Appropriate controls were included and results were expressed as the concentration of test compound required to inhibit cell growth by 50% relative to untreated controls (SRB $IC_{50}$).

The Activity Index (AI), a measure of the selectivity of the CHK1 inhibitor test compounds for effecting CHK1-dependent checkpoint abrogation versus cytotoxicity was calculated from the ratio of the CHK1 inhibitor cytotoxicity $IC_{50}$ versus the MIA $IC_{50}$ (i.e., AI=CHK1 inhibitor SRB $IC_{50}$/MIA $IC_{50}$), both measured in HT29 cells.

Assay 4: Cellular Efficacy in HT29 or SW620 Colon Carcinoma Cells in Combination with SN38 or Gemcitabine The ability of CHK1 inhibitor compounds to enhance SN38 (the active metabolite of the topoisomerase-I inhibitor irinotecan) and gemcitabine (an antimetabolite) cytotoxicity was assessed using a 96 hour sulforhodamine B assay (SRB, Sigma cat# S9012). HT29 or SW620 cells were seeded at 1.6 to $3.2 \times 10^3$ cells per well in 96-well plates in a volume of 160 µL medium and allowed to attach for 36 hours prior to treatment. Potentiation assays involved adding a fixed SRB $IC_{50}$ concentration of either gemcitabine or SN38 (determined using the methods in Assay 3 above) in a volume of 20 µL of medium (10× final concentration), to each well in quadruplicate and mixing for 1 minute. CHK1 inhibitor test compound (10 mM stock) was serially diluted from a starting concentration of 50 µM in medium and 20 µL was added per well in quadruplicate to give a final concentration range of 5 to 0.039 µM (8 concentrations) and mixed for 1 minute prior to incubation at 37° C. in a humidified atmosphere of 37° C. for 96 hours (four doublings) prior to fixing and SRB staining. Untreated and genotoxic alone treated controls were included and results were expressed as the concentration of CHK1 inhibitor required to inhibit cell growth by 50% (Potentiation $IC_{50}$).

The Potentiation Index (PI) was calculated as a measure of the ability of the CHK1 inhibitor to enhance SN38 or gemcitabine cytotoxicity and was defined as the ratio of the Cytotoxicity $IC_{50}$ of the CHK1 inhibitor alone versus the Potentiation $IC_{50}$ of the CHK1 inhibitor combined with the genotoxic (i.e., PI=CHK1 inhibitor SRB $IC_{50}$/Potentiation $IC_5O$.

Assay 5: Oral Bioavailability and Pharmacokinetics in Mice

All work was performed in accordance with the Home Office regulations under the Animals (Scientific Procedures) Act 1986 and according to UKCCCR guidelines for animal experimentation.

CHK1 inhibitor compounds were formulated in 10% DMSO, 1% Tween 20 and 89% sterile saline. Female Balb/c mice (Charles River UK Ltd, Margate, U.K.) were administered intravenously (iv) and orally (po) with 10 mg/kg of CHK1 inhibitor compound. Control animals received the vehicle alone. Groups of 3 mice were injected per timepoint. At 5, 15 and 30 minutes and 1, 2, 4, 6 and 24 hours after dosing, blood was collected by cardiac puncture with heparinised syringes from mice under anaesthesia (halothane/oxygen mix). Following centrifugation (9000×g, 2 minutes, 4° C.) plasma was frozen on dry ice and stored at −80° C. Tissues were excised, snap frozen in liquid nitrogen and stored at −80° C. Thawed plasma samples were extracted by protein precipitation using 3 volumes of methanol containing internal standard. Calibration standards (2 to 10000 nM in plasma) and QCs were prepared by spiking blank plasma matrix with the CHK1 inhibitor compound and extracting as per the test samples. After centrifugation, supernatant was transferred for analysis. Extracted plasma samples were analysed by LC-MS-MS on an Agilent 1200 or 1290 LC coupled to an Agilent 6410 triple quadrupole mass spectrometer for the quantitation of the CHK1 inhibitor compound and internal standard. Compounds were separated on a Phenomenex Kinetex C18 analytical column (50×2.1 mm, 2.6 μm) held at 55° C. The mobile phase consisted of 10 mM ammonium acetate and methanol at a flow rate of 0.4 mL/min. A 7 minute gradient was used to separate the analytes. Electrospray ionisation in positive ion mode was used and compounds were detected by MRM with the appropriate transition monitored (for example for Compound 1 being 380.2 to 320.3, with a fragmentor voltage of 154 V and collision energy of 20 V.

Non-compartmental pharmacokinetic analysis (models 200 and 201) was performed with Pharsight WinNonlin software (version 5.2.1).

Biological Data

Data for Compound 1 and Compound 2, obtained using the assays described above, are summarised in the following table.

A comparison of CHK1 $IC_{50}$ data (obtained via Assay 1 above) for Compounds 1 and 2 with corresponding data obtained for the 16 similar compounds shown in Collins et al., 2009a (obtained using a DELFIA Assay as described in Collins et al., 2009a) is provided in the following table.

TABLE 3

| # | Compound | CHK1 $IC_{50}$ (nM) |
|---|---|---|
|  | Compound 1 | 1.4 |
|  | Compound 2 | 2.1 |
| 1 | Y-154 | 1 |
| 2 | Y-081 | 2 |
| 3 | Y-152 | 2 |
| 4 | Y-158 | 2 |
| 5 | Y-147 | 4 |
| 6 | Y-153 | 4 |
| 7 | Y-155 | 5 |
| 8 | Y-149 | 10 |
| 9 | Y-156 | 10 |
| 10 | Y-146 | 11 |
| 11 | Y-148 | 13 |
| 12 | Y-157 | 15 |
| 13 | Y-150 | 17 |
| 14 | Y-102 | 20 |
| 15 | Y-159 | 23 |
| 16 | Y-151 | 24 |

A comparison of CHK1 Cellular Potency MIA data (obtained via Assay 2 above) for Compounds 1 and 2 with the corresponding data obtained for the 16 similar compounds shown in Collins et al., 2009a is provided in the following table.

TABLE 2

| Compound | Compound 1 | Compound 2 |
|---|---|---|
| Structure | (structure) | (structure) |
| Assay 1: CHK1 $IC_{50}$ (nM) | 1.4 (±0.3, n = 3) | 2.1 (±0.5) |
| Assay 2: CHK1 Cellular Potency MIA $IC_{50}$ (nM) | 30 (±12, n = 6) | 18 (±7.5, n = 3) |
| Assay 3: Cellular Selectivity (Activity Index; fold) | 26.4 (±8.6, n = 6) | 150 (±85, n = 3) |
| Assay 4: Cell Efficacy + SN38 in HT29 cells (Potentiation Index; fold) | 1.8 (±0.3, n = 3) | — |
| Assay 4: Cell Efficacy + Gemcitabine in SW620 cells (Potentiation Index; fold) | 16.9 (±3.4, n = 7) | 8.1 (±3.6, n = 3) |
| Assay 5: Oral Bioavailability in Mouse (%) | 105 | — |

TABLE 4

| # | Compound | CHK1 Cellular Potency MIA IC$_{50}$ (nM) | (fold better) Compound 1 | (fold better) Compound 2 |
|---|---|---|---|---|
|  | Compound 1 | 30 | — | — |
|  | Compound 2 | 18 | — | — |
| 1 | Y-154 | 90 | ~3 | ~5 |
| 2 | Y-155 | 120 | ~4 | ~7 |
| 3 | Y-153 | 180 | ~6 | ~10 |
| 4 | Y-158 | 280 | ~9 | ~15 |
| 5 | Y-081 | 310 | ~10 | ~17 |
| 6 | Y-150 | 390 | ~13 | ~22 |
| 7 | Y-152 | 400 | ~13 | ~22 |
| 8 | Y-156 | 560 | ~19 | ~31 |
| 9 | Y-157 | 600 | ~20 | ~33 |
| 10 | Y-159 | 700 | ~23 | ~39 |
| 11 | Y-151 | 800 | ~27 | ~44 |
| 12 | Y-102 | 800 | ~27 | ~44 |
| 13 | Y-147 | 900 | ~30 | ~50 |
| 14 | Y-148 | 900 | ~30 | ~50 |
| 15 | Y-149 | 1100 | ~34 | ~61 |
| 16 | Y-146 | 1500 | ~50 | ~83 |

It is clear that Compounds 1 and 2 have outstanding CHK1 cellular potency (MIA Assay). High cellular potency for inhibition of CHK1 is critical for the development of a CHK1 inhibitor. Compounds 1 and 2 have substantially higher cellular potency for CHK1-mediated effects than all of the 16 compounds, and are approximately 3-fold and 5-fold, respectively, more potent than the next most potent compound (Y-154).

A comparison of Cellular Selectivity data (obtained via Assay 3 above) for Compounds 1 and 2 with the corresponding data obtained for the 16 similar compounds shown in Collins et al., 2009a is provided in the following table.

TABLE 5

| # | Compound | Cellular Selectivity (fold) | (fold better) Compound 1 | (fold better) Compound 2 |
|---|---|---|---|---|
|  | Compound 1 | 26 | — | — |
|  | Compound 2 | 150 | — | — |
| 1 | Y-155 | 11 | ~2.4 | ~13 |
| 2 | Y-150 | 10 | ~2.6 | ~15 |
| 3 | Y-159 | 9.9 | ~2.6 | ~15 |
| 4 | Y-153 | 9.2 | ~2.8 | ~16 |
| 5 | Y-154 | 9.0 | ~2.9 | ~17 |
| 6 | Y-157 | 6.3 | ~4.1 | ~24 |
| 7 | Y-151 | 6.0 | ~4.3 | ~25 |
| 8 | Y-156 | 5.4 | ~4.8 | ~28 |
| 9 | Y-102 | 4.6 | ~5.6 | ~33 |
| 10 | Y-146 | 4.5 | ~5.8 | ~33 |
| 11 | Y-148 | 4.4 | ~5.9 | ~34 |
| 12 | Y-147 | 4.3 | ~6.0 | ~35 |
| 13 | Y-158 | 4.3 | ~6.0 | ~35 |
| 14 | Y-149 | 3.5 | ~7.4 | ~43 |
| 15 | Y-152 | 3.5 | ~7.4 | ~43 |
| 16 | Y-081 | 3.5 | ~7.4 | ~43 |

It is clear that Compounds 1 and 2 have outstanding cellular selectivity, measured as the ratio between CHK1 cellular potency (MIA assay) and non-specific cytotoxicity in a growth inhibition assay. Cellular selectivity for CHK1 mediated effect versus non-specific cytotoxicity is important for development of a CHK1 inhibitor in order to maximise the therapeutic window. Compounds 1 and 2 are approximately 26-fold selective and 150-fold selective, respectively, whereas the next most selective compound is only approximately 11-fold selective (Y-155).

A comparison of Cellular Efficacy data (obtained via Assay 4 above) for Compounds 1 and 2 with the corresponding data obtained for many of the 16 similar compounds shown in Collins et al., 2009a is provided in the following tables.

TABLE 6

| # | Compound | Cell Efficacy + SN38 HT29 (fold) |
|---|---|---|
|  | Compound 1 | 1.8 |
|  | Compound 2 | n/a |
| 1 | Y-157 | 2 |
| 2 | Y-150 | 2 |
| 3 | Y-156 | 1.6 |
| 4 | Y-151 | 1.5 |
| 5 | Y-159 | 1.3 |
| 6 | Y-081 | 1.2 |
| 7 | Y-153 | 1 |
| 8 | Y-155 | 0.9 |
| 9 | Y-154 | 0.8 |
| 10 | Y-152 | 0.7 |
| 11 | Y-147 | n/a |
| 12 | Y-158 | n/a |
| 13 | Y-146 | n/a |
| 14 | Y-148 | n/a |
| 15 | Y-149 | n/a |
| 16 | Y-102 | n/a |

TABLE 7

| # | Compound | Cell Efficacy + Gemcitabine SW620 (fold) |
|---|---|---|
|  | Compound 1 | 17 |
|  | Compound 2 | 8.1 |
| 1 | Y-157 | n/a |
| 2 | Y-150 | 4.8 |
| 3 | Y-156 | n/a |
| 4 | Y-151 | n/a |
| 5 | Y-159 | n/a |
| 6 | Y-081 | n/a |
| 7 | Y-153 | 8.6 |
| 8 | Y-155 | n/a |
| 9 | Y-154 | n/a |
| 10 | Y-152 | 8 |
| 11 | Y-147 | n/a |
| 12 | Y-158 | n/a |
| 13 | Y-146 | n/a |
| 14 | Y-148 | n/a |
| 15 | Y-149 | n/a |
| 16 | Y-102 | n/a |

It is clear that Compounds 1 and 2 have outstanding cellular efficacy, measured as the ability to sensitize cells to two representative genotoxic therapeutic agents: SN38 and gemcitabine. A value of >1 is essential for a developable compound (otherwise the compound acts to reduce the effect of the genotoxic therapy).

Compound 1 has almost the highest potentiation for SN38 (approximately 1.8-fold) and the highest potentiation for gemcitabine (approximately 17-fold), indicating a robust efficacy. The most potentiating compound for SN38 is Y-150 (approximately 2-fold), which has only approximately 4.8-fold potentiation for gemcitabine. The next most potentiating compound for gemcitabine is Y-153 (approximately 8.6-fold), which has no potentiation (i.e., approximately 1-fold) for SN38.

In addition, Compound 1 has outstanding oral bioavailability in mice: 100% (reported as "105%" in the table above).

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of publications are cited herein in order to more fully describe and disclose the invention and the state of the art to which the invention pertains. Full citations for these publications are provided below. Each of these publications is incorporated herein by reference in its entirety into the present disclosure, to the same extent as if each individual publications was specifically and individually indicated to be incorporated by reference.

Almeida et al., 2008, "Pyrazolyl-amino-substituted pyrazines and their use for the treatment of cancer", international (PCT) patent publication number WO 2008/117050 A1 published 2 Oct. 2008.

Balaint and Vousden, 2001, "Activation and activities of the p53 tumour suppressor protein," *Br. J. Cancer*, Vol. 85, pp. 1813-1823.

Bartek and Lukas, 2003, "Chk1 and Chk2 kinases in checkpoint control and cancer," *Cancer Cell*, Vol. 3, pp. 421-429.

Brooks et al., 2012, "A potent chk1 inhibitor is selectively toxic in melanomas with high levels of replicative stress," *Oncogene*, doi:10.1038/onc.2012.72.

Carson and Lois, 1995, "Cancer progression and p53," *Lancet*, Vol. 346, pp. 1009-1011.

Cavelier et al., 2009, "Constitutive activation of the DNA damage signaling pathway in acute myeloid leukemia with complex karyotype: Potential importance for checkpoint targeting therapy," *Cancer Res.*, Vol. 69, pp. 8652-8661.

Cole et al., 2011 "RNAi screen of the protein kinome identifies checkpoint kinase 1 (chk1) as a therapeutic target in neuroblastoma," *Proc. Natl. Acad. Sci. U.S.A.*, Vol. 108, pp. 3336-3341.

Collins et al., 2009a, "Pyrazin-2-yl-2-yl-amine and pyrazin-2-yl-pyrimidin-4-yl-amine compounds and their use", international (PCT) patent publication number WO 2009/044162 A1 published 9 Apr. 2009.

Collins et al., 2009b, "Bicyclylaryl-aryl-amine compounds and their use", international (PCT) patent publication number WO 2009/103966 A1 published 27 Aug. 2009.

Davies et al., 2011, "Single-agent inhibition of chk1 is antiproliferative in human cancer cell lines in vitro and inhibits tumor xenograft growth in vivo," *Oncol. Res.*, Vol. 19, pp. 349-363.

Di Micco et al., 2006, "Oncogene-induced senescence is a DNA damage response triggered by DNA hyper-replication," *Nature*, Vol. 444, pp. 638-642.

Dixon and Norbury, 2002, "Therapeutic exploitation of checkpoint defects in cancer cells lacking p53 function," *Cell Cycle*, Vol. 1, pp. 362-368.

Ferrao et al., 2011, "Efficacy of chk inhibitors as single agents in myc-driven lymphoma cells," *Oncogene*, doi: 10.1038/onc.2011.358.

Greenblatt et al., 1994, "Mutations in the p53 tumor suppressor gene: clues to cancer etiology and molecular pathogenesis," *Cancer Res.*, Vol. 54, pp. 4855-4878.

Guzi et al., 2011, "Targeting the replication checkpoint using SCH 900776, a potent and functionally selective CHK1 inhibitor identified via high content screening," *Mol. Cancer Ther.*, Vol. 10, pp. 591-602.

Höglund et al., 2011, "Therapeutic Implications for the Induced Levels of Chk1 in Myc-Expressing Cancer Cells," *Clin. Cancer Res.*, Vol. 17, pp. 7067-7079.

Ioannidis et al., 2009, "Discovery of pyrazol-3-ylamino pyrazines as novel JAK2 inhibitors", *Bioorq. Med. Chem. Lett.*, Vol. 19, pp. 6524-6528.

Lainchbury et al., 2012, "Discovery of 3-alkoxyamino-5-(pyridin-2-ylamino)pyrazine-2-carbonitriles as selective, orally bioavailable CHK1 inhibitors", *J. Med. Chem.*, Vol. 55, No. 22, pp. 10229-10240.

Li et al., 2007, "Synthesis and in-vitro biological activity of macrocyclic urea CHK1 inhibitors", *Bioorg. Med. Chem. Lett.*, Vol. 17, pp. 6499-6504.

Lin et al., 2005, "Macrocyclic kinase inhibitors", US patent publication number US 2005/0215556 A1 published 29 Sep. 2005.

Liu et al., 2000, "Chk1 is an essential kinase that is regulated by Atr and required for the G(2)/M DNA damage checkpoint," *Genes Dev.*, Vol. 14, pp. 1448-1459.

Murga et al., 2011, "Exploiting oncogene-induced replicative stress for the selective killing of Myc-driven tumors," *Nat. Struct. Mol. Biol.*, Vol. 18, pp. 1331-1335.

Sanchez et al., 1997, "Conservation of the Chk1 checkpoint pathway in mammals: linkage of DNA damage to Cdk regulation through Cdc25," *Science*, Vol. 277, pp. 1497-1501.

Sorensen et al., 2005, "Cell-cycle checkpoint kinase Chk1 is required for mammalian homologous recombination repair," *Nat. Cell Biol.*, Vol 7, pp. 195-201.

Tao et al., 2005, "Macrocyclic kinase inhibitors", international (PCT) patent publication number WO 2005/047294 A1 published 26 May 2005.

Tao et al., 2006, "Chk1 inhibitors for novel cancer treatment," *Anti-Cancer Agents in Medicinal Chemistry*, Vol. 6, pp. 377-388.

Tao et al., 2007a, "Macrocyclic ureas as potent and selective CHK1 inhibitors: an improved synthesis, kinome profiling, structure-activity relationships, and preliminary pharmacokinetics," *Bioorq. Med. Chem. Lett.*, Vol. 17, pp. 6593-6601.

Tao et al., 2007b, "Structure-based design, synthesis, and biological evaluation of potent and selective macrocyclic checkpoint kinase 1 inhibitors," *J. Med. Chem.*, Vol. 50, pp. 1514-1527.

Walton et al., 2010, "The preclinical pharmacology and therapeutic activity of the novel CHK1 inhibitor SAR-020106," *Mol. Cancer Ther.*, Vol. 9, No. 1, pp. 89-100.

Walton et al., 2012, "CCT244747 is a novel potent and selective CHK1 inhibitor with oral efficacy alone and in combination with genotoxic anticancer drugs", *Clin. Cancer Res.*, Vol. 18, No. 20, pp. 5650-5661.

Wang et al., 1996, "UCN-01: a potent abrogator of G2 checkpoint function in cancer cells with disrupted p53," *J. Natl. Cancer Inst.*, Vol. 8, pp. 956-965.

Weinert and Hartwell, 1989, "Control of G2 delay by the rad9 gene of *Saccharomyces cerevisiae*," *J. Cell Sci. Suppl.*, Vol. 12, pp. 145-148.

Xiao et al., 2006, "Differential roles of checkpoint kinase 1, checkpoint kinase 2, and mitogen-activated protein kinase-activated protein kinase 2 in mediating DNA damage-induced cell cycle arrest: implications for cancer therapy," *Mol. Cancer Ther.*, Vol. 5, pp. 1935-1943.

Zachos et al., 2003, "Chk1-deficient tumour cells are viable but exhibit multiple checkpoint and survival defects," *EMBO J.*, Vol. 22, pp. 713-723.

Zhao et al., 2002, "Disruption of the checkpoint kinase 1/cell division cycle 25A pathway abrogates ionizing radiation-induced S and G2 checkpoints," *Proc. Natl. Acad. Sci. USA*, Vol. 99, pp. 14795-14800.

The invention claimed is:

1. A compound according to formula II, or a salt thereof:

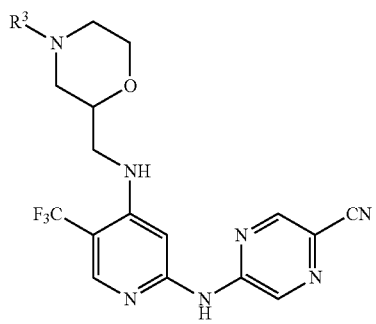

wherein
$R^3$ is

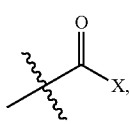

where X is an alkyl or alkoxy organic functional group.

2. The compound of claim 1, wherein X is selected from the group consisting of: methyl (—CH$_3$), benzyloxy (—OCH$_2$C$_6$H$_5$), t-butoxy (—OC(CH$_3$)$_3$), 2-trimethylsilyl-ethyloxy, and allyloxy.

3. The compound of claim 1, wherein X is t-butoxy (—OC(CH$_3$)$_3$).

4. A compound of formula III, or a salt thereof:

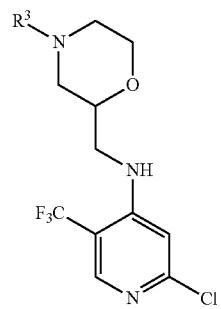

wherein
$R^3$ is hydrogen or is

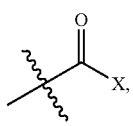

where X is an alkyl or alkoxy organic functional group.

5. The compound of claim 4, wherein $R^3$ is hydrogen.

6. The compound of claim 4, wherein the compound is according to the following structure, or salt thereof:

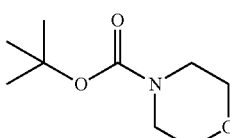

7. A process for manufacturing a compound according to the following structure, or a salt thereof:

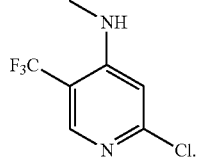

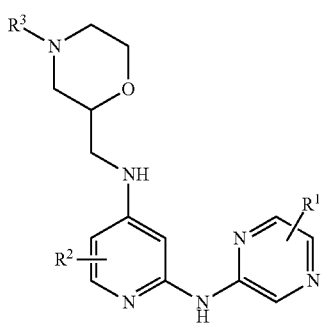

wherein
R¹ is CN;
R² is CF₃;
R³ is

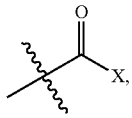

where X is an alkyl or alkoxy organic functional group;
the process comprising using cross coupling reaction conditions to couple a compound of the structure:

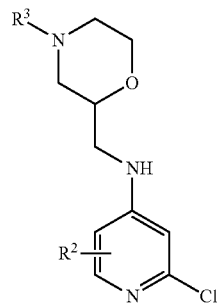

to a compound of the structure

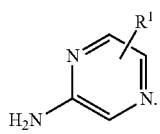

8. The process of claim 7, wherein the reaction conditions are as follows:

suspending: the

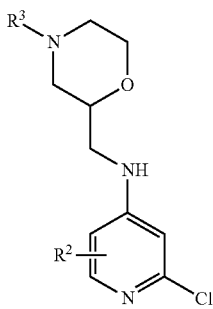

compound, the

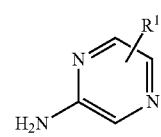

compound, an organic phosphine compound, cesium carbonate, and a palladium(0) compound in an aprotic organic solvent;
and heating the suspension;
wherein R¹, R² and R³ are as defined in claim 7.

9. The process of claim 7, wherein the heating is at about 100° C.

10. The process of claim 7, wherein the heating lasts for about 24 hours.

11. The process of claim 7, wherein R³ is

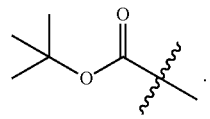 [SMILES: *C(=O)OC(C)(C)C]

12. The process of claim 7, wherein R³ is

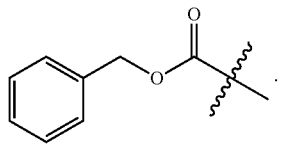 [SMILES: *C(=O)OCc1ccccc1]

13. The compound of claim 1, wherein X is methyl (—CH₃).

14. The compound of claim 1, wherein X is benzyloxy (—OCH₂C₆H₅).

15. The compound of claim 1, wherein X is 2-trimethyl-silylethyloxy.

16. The compound of claim 1, wherein X is allyloxy.

* * * * *

SEQUENCE LISTING

```
<160> NUMBER OF SEQ ID NOS: 1

<210> SEQ ID NO 1
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Lys Lys Val Ser Arg Ser Gly Leu Tyr Arg Ser Pro Ser Met Pro
1               5                   10                  15

Glu Asn Leu Asn Arg Pro Arg
            20
```